(12) United States Patent  
Lerner

(10) Patent No.: US 10,583,292 B2  
(45) Date of Patent: Mar. 10, 2020

(54) ELECTRONIC NEUROMODULATORY EMULATION OF EXTRA- AND INTRA-AORTIC BALLOON PUMP COUNTER-PULSATION SYSTEMS AND METHODS

(71) Applicant: CHF Solutions, Inc., Eden Prairie, MN (US)

(72) Inventor: David Lerner, St. Paul, MN (US)

(73) Assignee: CHF Solutions, Inc., Eden Prairie, MN (US)

(*) Notice: Subject to any disclaimer, the term of this patent is extended or adjusted under 35 U.S.C. 154(b) by 84 days.

(21) Appl. No.: 15/786,775

(22) Filed: Oct. 18, 2017

(65) Prior Publication Data

US 2018/0104491 A1     Apr. 19, 2018

Related U.S. Application Data

(60) Provisional application No. 62/409,623, filed on Oct. 18, 2016.

(51) Int. Cl.
*A61N 1/36*        (2006.01)
*A61M 1/10*        (2006.01)
(Continued)

(52) U.S. Cl.
CPC ......... *A61N 1/36114* (2013.01); *A61M 1/106* (2013.01); *A61M 1/107* (2013.01); *A61M 1/1072* (2013.01); *A61M 1/1086* (2013.01); *A61M 1/125* (2014.02); *A61N 1/0556* (2013.01); *A61N 1/36139* (2013.01); *A61M 1/122* (2014.02); *A61N 1/025* (2013.01); *A61N 1/0551* (2013.01)

(58) Field of Classification Search
CPC . A61N 1/36114; A61N 1/36053; A61M 1/122
See application file for complete search history.

(56) References Cited

U.S. PATENT DOCUMENTS

| 6,632,169 B2 | 10/2003 | Korakianitis et al. |
| 6,832,982 B1 | 12/2004 | Lapanashvili et al. |

(Continued)

FOREIGN PATENT DOCUMENTS

| EP | 2574352 | 4/2013 |
| EP | 3028739 | 6/2016 |

(Continued)

*Primary Examiner* — Alyssa M Alter
(74) *Attorney, Agent, or Firm* — Westman, Champlin & Koehler, P.A.

(57) ABSTRACT

An implantable electronic neuromodulation system includes an implantable pulse generator comprising a controller and a memory. The memory is configured to store an emulated neurosensory signal representative of nerve traffic acquired from a patient equipped with an extra-aortic balloon pump counter-pulsation system or an intra-aortic balloon pump counter-pulsation system. A lead is coupled to the implantable pulse generator. At least one electrode is coupled to the lead. The at least one electrode is positionable in contact with or adjacent to at least one nerve that carries sensory information from baroreceptors. The controller is configured to stimulate the at least one nerve using the emulated neurosensory signal.

20 Claims, 15 Drawing Sheets

(51) Int. Cl.
*A61M 1/12* (2006.01)
*A61N 1/05* (2006.01)
*A61N 1/02* (2006.01)

(56) References Cited

U.S. PATENT DOCUMENTS

| | | |
|---|---|---|
| 7,740,575 B2 | 6/2010 | Peters et al. |
| 7,765,003 B2 | 7/2010 | Peters et al. |
| 7,955,248 B2 | 6/2011 | Miller |
| 8,777,833 B2 | 7/2014 | Peters et al. |
| 9,119,908 B2 | 9/2015 | Peters et al. |
| 2004/0097783 A1 | 5/2004 | Peters et al. |
| 2004/0097784 A1 | 5/2004 | Peters et al. |
| 2006/0074453 A1* | 4/2006 | Kieval ............... A61N 1/36114 607/9 |
| 2006/0089678 A1 | 4/2006 | Shalev |
| 2010/0179374 A1 | 7/2010 | Stephens |
| 2012/0220816 A1 | 8/2012 | Peters et al. |
| 2013/0171599 A1* | 7/2013 | Bleich ............... A61B 5/0456 434/247 |

FOREIGN PATENT DOCUMENTS

| | | |
|---|---|---|
| WO | WO9208500 | 5/1992 |
| WO | WO9707849 | 3/1997 |
| WO | WO9904833 | 2/1999 |
| WO | WO2005042063 | 5/2005 |
| WO | WO2005042089 | 5/2005 |
| WO | WO2017040218 | 3/2017 |

* cited by examiner

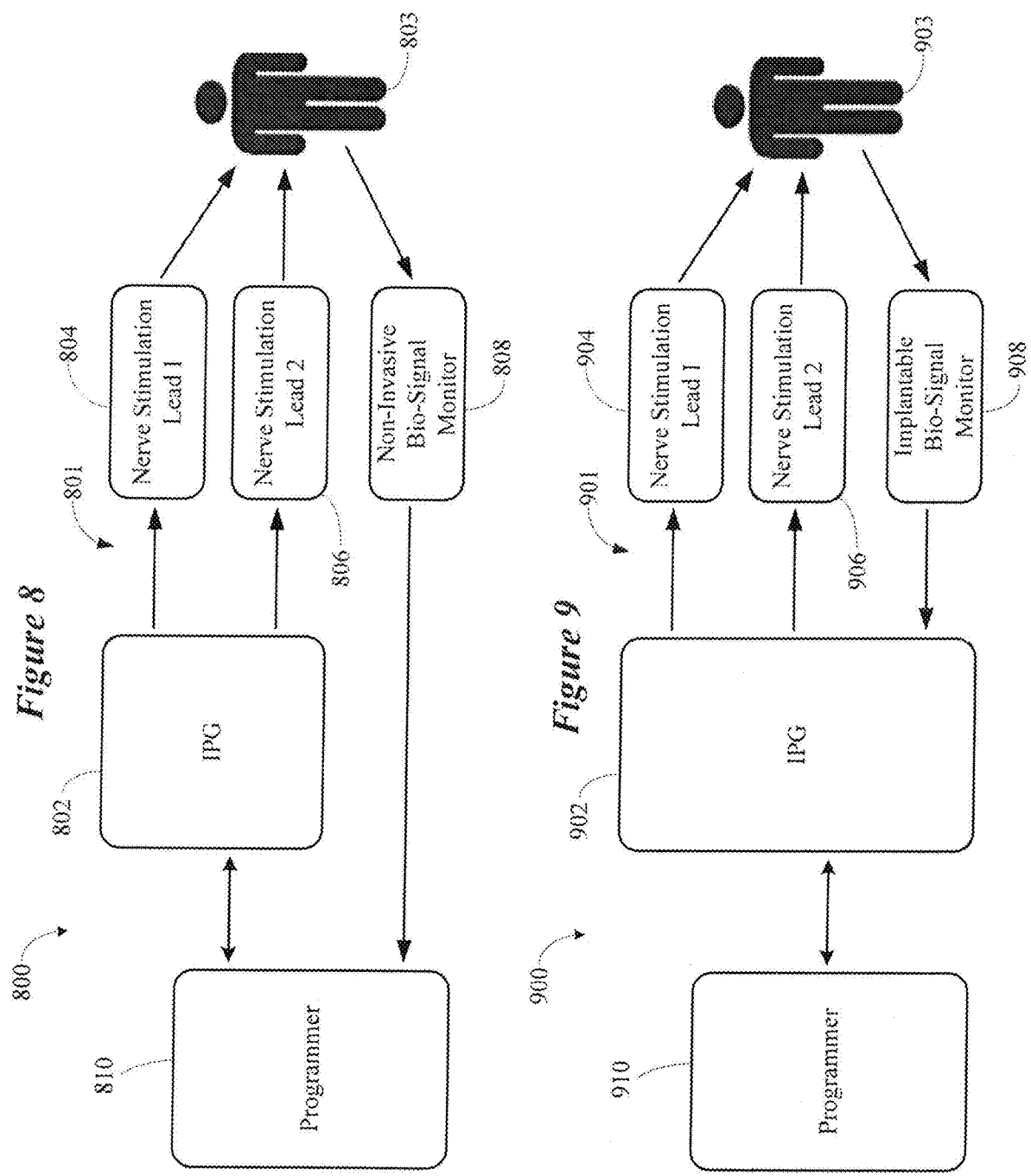

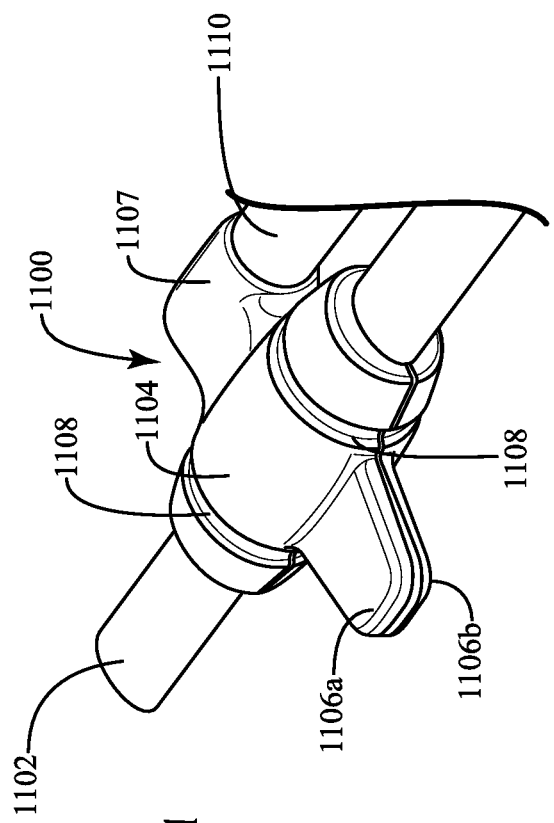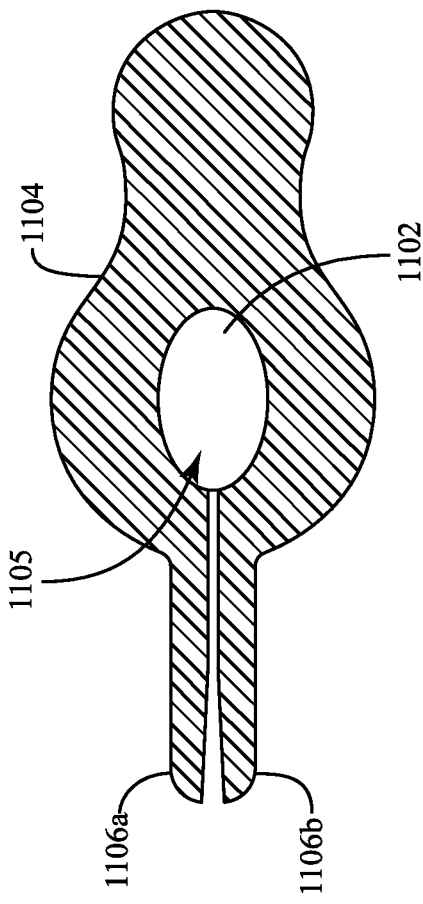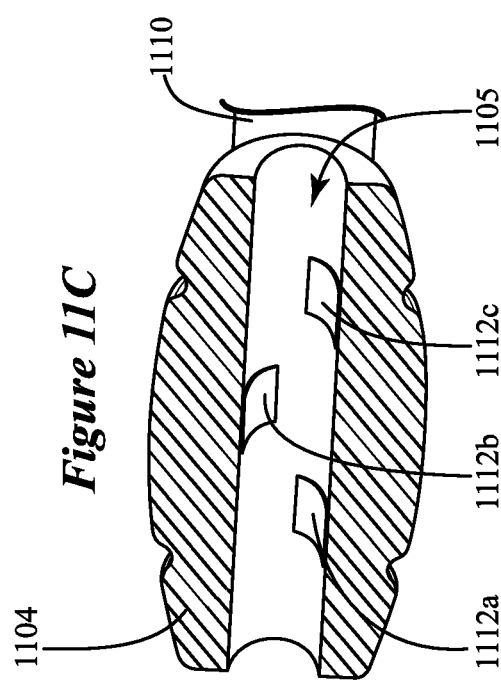
*Figure 11A*
*Figure 11B*
*Figure 11C*

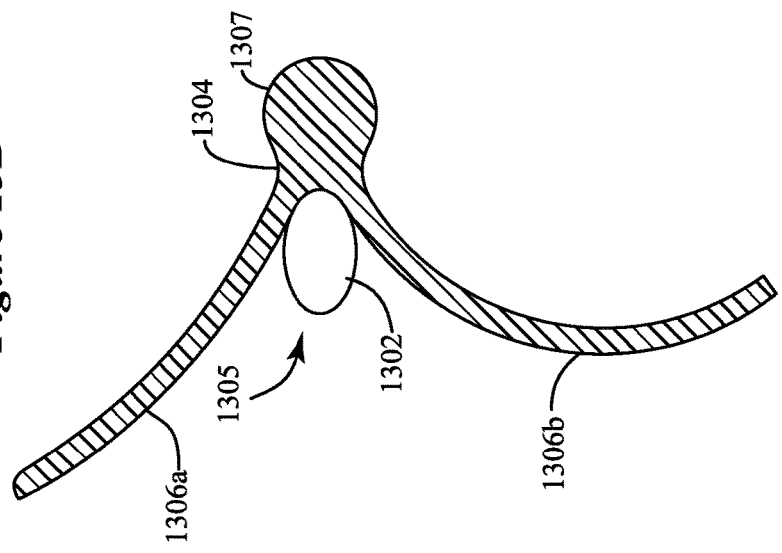
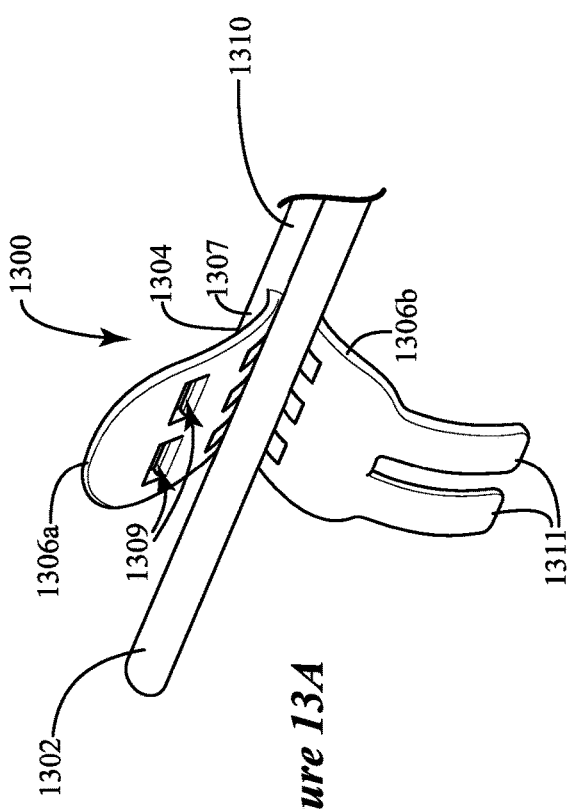
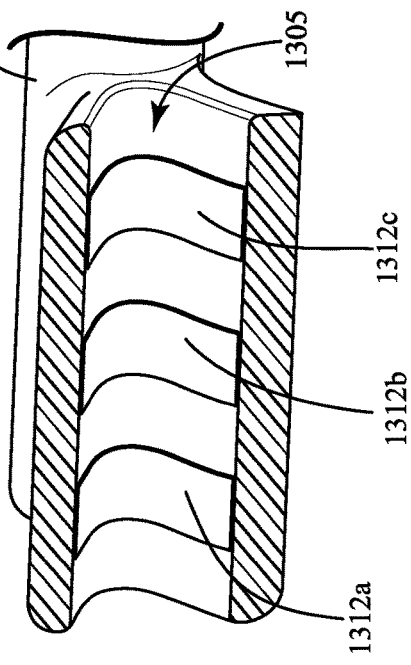
Figure 13B
Figure 13A
Figure 13C

ELECTRONIC NEUROMODULATORY EMULATION OF EXTRA- AND INTRA-AORTIC BALLOON PUMP COUNTER-PULSATION SYSTEMS AND METHODS

RELATED PATENT DOCUMENTS

This application claims the benefit of Provisional Patent Application Ser. No. 62/409,623, filed on Oct. 18, 2016, to which priority is claimed pursuant to 35 U.S.C. § 119(e) and which is hereby incorporated herein by reference.

SUMMARY

Various embodiments of the disclosure are directed to a system comprising an implantable electronic neuromodulation system including an implantable pulse generator comprising a controller and a memory. The memory is configured to store an emulated neurosensory signal representative of nerve traffic acquired from a patient equipped with an extra-aortic balloon pump counter-pulsation system or an intra-aortic balloon pump counter-pulsation system. A lead is coupled to the implantable pulse generator. At least one electrode is coupled to the lead. The at least one electrode is positionable in contact with or adjacent to at least one nerve that carries sensory information from baroreceptors. The controller is configured to stimulate the at least one nerve using the emulated neurosensory signal.

Some embodiments of the disclosure are directed to a method comprising storing, in an implantable electronic neuromodulation system, an emulated neurosensory signal representative of nerve traffic acquired from a patient equipped with an extra-aortic balloon pump counter-pulsation system or an intra-aortic balloon pump counter-pulsation system. The method comprises sensing occurrence of a diastolic phase of a patient's heart. The method also comprises stimulating, during the diastolic phase, at least one nerve that carries sensory information from baroreceptors using the emulated neurosensory signal.

Other embodiments of the disclosure are directed to a system comprising an implantable stimulation source including a controller configured to control delivery of electrical stimulation modeled to emulate an extra-aortic balloon pump counter-pulsation system or an intra-aortic balloon pump counter-pulsation system. A lead is coupled to the stimulation source, and at least one electrode is coupled to the lead. The at least one electrode is positionable in contact with or adjacent to at least one nerve.

The above summary is not intended to describe each disclosed embodiment or every implementation of the present disclosure. The figures and the detailed description below more particularly exemplify illustrative embodiments.

BRIEF DESCRIPTION OF THE DRAWINGS

FIG. 8 illustrates a system and method for adjusting and calibrating an electronic neuromodulation system in accordance with various embodiments;

FIG. 9 illustrates a system and method for adjusting and calibrating an electronic neuromodulation system in accordance with various embodiments;

FIGS. 11A-11C illustrate a multi-electrode nerve cuff in accordance with various embodiments;

FIGS. 13A-13C illustrate a multi-electrode nerve cuff in accordance with various embodiments;

The figures are not necessarily to scale. Like numbers used in the figures refer to like components. However, it will be understood that the use of a number to refer to a component in a given figure is not intended to limit the component in another figure labeled with the same number.

DESCRIPTION

Figure 1:
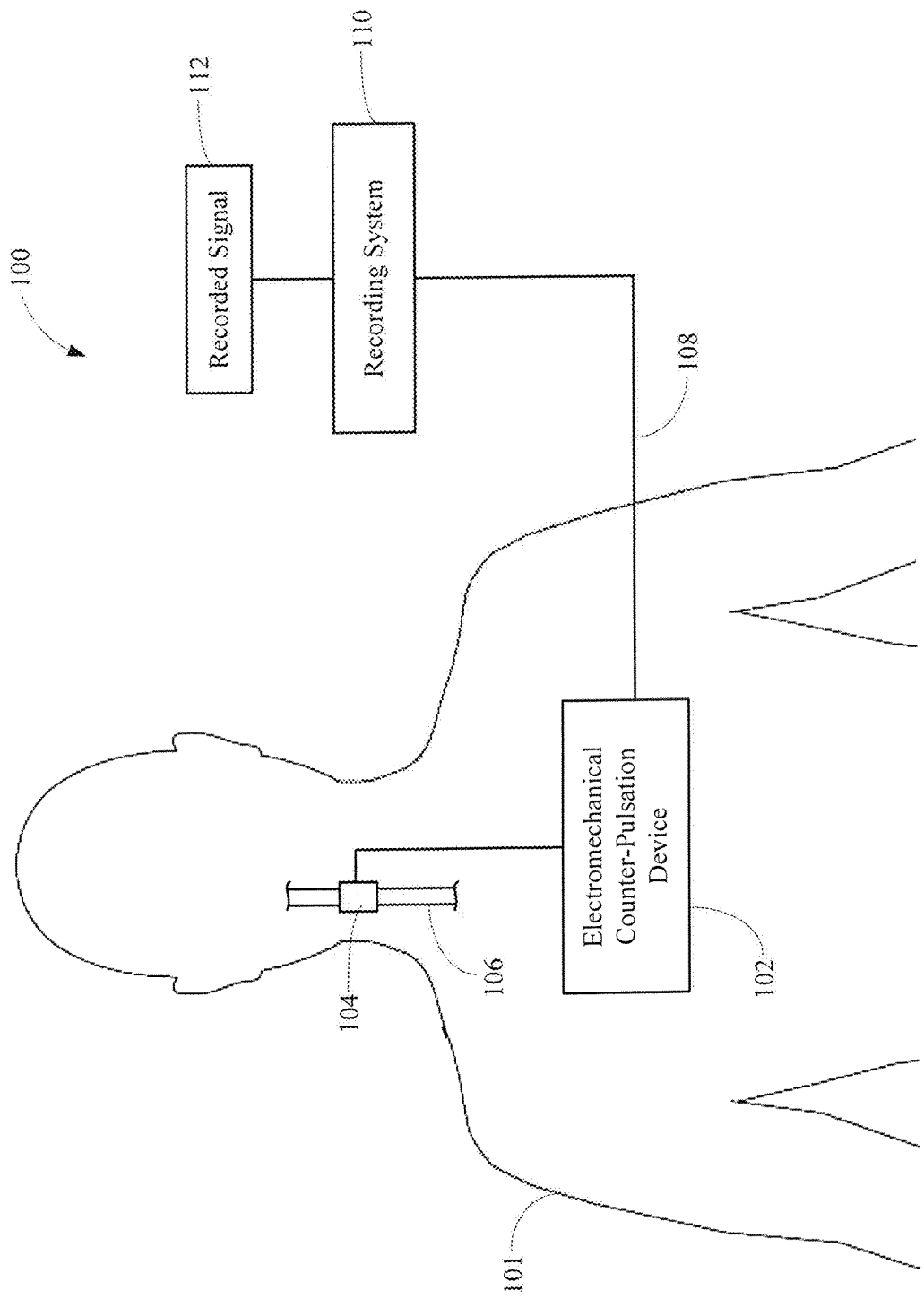
FIG. 1 illustrates a system configured to acquire and record a signal representative of nerve traffic acquired from a patient equipped with an electromechanical counter-pulsation device in accordance with various embodiments.

Embodiments of the disclosure are directed to an electronic neuromodulation system configured to deliver therapy to patients who are experiencing one or more of heart failure, hypertension, or chronic kidney disease. Various systems and methods described in this disclosure can include attributes intended to potentiate that therapy by emulating the function of electromechanical neuromodulation employed by extra-aortic and intra-aortic balloon counter-pulsation systems. The techniques described herein can include a number of advantages intended to deliver the benefits of counter-pulsation without its concomitant deleterious effects (e.g. stress on aorta, high level of intracorporeal invasiveness, high power utilization, etc.). In several of the illustrative embodiments, extra-aortic counter-pulsation is referenced but intra-aortic counter-pulsation may also be referenced without departing from the scope of the disclosure.

Electromechanical counter-pulsation systems function by compressing the ascending aorta in synchrony with cardiac function. Specifically, the counter-pulsation system measures one or more aspects of heart function (e.g. R wave on an electrogram (EGM), heart valve action via acoustic sensor, etc.) to determine when in the cardiac cycle to compress the aorta. For example, an extra-aortic balloon can be inflated and the aorta compressed during diastole and the balloon can be deflated prior to ventricular contraction and systole. When the aorta is compressed during diastole, transmural blood pressure in the aorta is transiently elevated leading to baroreceptor stimulation in the aorta in particular and arterial tree in general. The baroreceptors in the aorta may be stimulated due to the elevated pressure indirectly and due to the balloon compression directly. The stimulation of the aortic and arterial baroreceptors can lead to altered neural traffic (action potential signals) in various afferent nerve fibers including but not limited to the Vagus nerve (VN), Carotid Sinus nerve (CSN), and Aortic Depressor nerve (ADN). This neural traffic can be conveyed to medullary (and other) centers of the brain leading to efferent neural traffic conveyed through multiple pathways to vessels and organs. The physiological results of this traffic may include reduction in heart rate, vasodilation, reduction in blood pressure, and reduced heart contractility. Importantly, some of these physiological effects will alter arterial pulse wave velocity and the nature of arterial pulse wave reflections from distal points in the arterial tree back to the aorta. In effect, there can be a multi-path system starting with baroreceptor stimulation that leads to changes in cardio and peripheral vascular function and status that is helpful for patients with heart failure, hypertension, and chronic kidney disease.

Embodiments of the disclosure are directed to techniques that can accomplish by electronic neuromodulation techniques what extra- and intra-aortic balloon counter-pulsation systems accomplish by electromechanical techniques. Described are a number of unique aspects of various embodiments apart from the core concept of electronic neuromodulation emulation of electromechanical counter-pulsation. One core construct of the emulation of electromechanical counter-pulsation effects via electronic neural stimulation relates to the nature of the stimulation signal, referred to herein as an emulated neurosensory signal. The second core construct can relate to the timing and extent of the application of that signal to the target nerve via electrodes. The third core construct relates to the target nerves themselves.

The first construct—the nature of the emulated neurosensory signal—relates to the amplitude, duty cycle, and frequency content that can allow for selective stimulation of those nerve fibers within a target nerve that carry sensor information arising from the baroreceptors as distinct from nerve fibers that may carry other afferent nerve traffic (e.g. from chemoreceptors). Non-selective stimulation may lead to unwanted side effects (e.g. pain, nausea, etc.) that can be deleterious to the patient experience. Existing techniques emphasize approaches to selective stimulation of nerve fibers via arrangement of electrodes, stimulation intensity, and focus of electric fields.

Various techniques of this disclosure can overcome the limitations of existing techniques by applying an emulated neurosensory signal to target nerves based on a pattern that is a recording or a derivative of signals generated by electromechanical counter-pulsation systems. Illustratively, nerve traffic in the Carotid Sinus nerve (CSN) from a patient with an implanted counter-pulsation device may be measured and recorded. This CSN signal may be programmed into an implantable pulse generator (IPG) and then be applied directly to the target nerve. The CSN signal can be modified to accommodate the heart rate and cardiac valve action of the patient receiving the emulated neurosensory signal.

Alternatively, a derivative signal from the recorded CSN signal may be applied to the target nerve. Illustratively and without limitation, a Fourier Transform or a parametric spectral analysis (e.g. Burg Transform, Welch Transform, Fast Fourier Transform) may be applied to the original, recorded CSN signal and the predominant harmonic frequencies identified. An inverse Fourier Transform may be applied to generate a new time domain signal that may then be applied to the target nerve. In another illustrative embodiment, an amplitude scaled version of the original recorded CSN signal may be applied to the target nerve. The derivative signal can be modified to accommodate the heart rate and cardiac valve action of the patient receiving the emulated neurosensory signal. In some example implementations, the stimulation pulse delivered by an IPG can include a rectangular pulse train with a fixed or variable amplitude, frequency, and duty cycle.

The second construct—relating to the timing and extent of the signal application to the target nerve—may involve a number of embodiments without departing from the scope of the disclosure. In some examples, the emulated neurosensory signal may be triggered by secondary semaphores of systole and diastole as is the case for some electromechanical counter-pulsation devices. For example, an electrogram (EGM) may be incorporated into the system and the resulting signal may be interpreted in real time to identify an R wave to trigger the stimulation activity. In this way, neural stimulation would only occur during diastole in an analogous approach to some electromechanical counter-pulsation devices. In a representative embodiment, an acoustic sensor may be employed to determine aortic valve status to ensure that stimulation activity is triggered only during diastole. In yet another illustrative example, an implanted ultrasound sensor may be applied to the aorta to determine the start of diastole and systole during the cardiac cycle to ensure that stimulation activity occurs only during diastole.

In other embodiments, measures of cardiovascular function may be measured to determine the timing and extent of neural stimulation. In one example implementation, heart rate may be measured via implanted EGM, ultrasound Doppler sensor, or optical sensor and the stimulation activity may be modulated by the heart rate (e.g., using a time stretching algorithm). In yet another approach, blood pressure may be measured by implanted or extracorporeal blood pressure sensors or systems to modulate the timing and extent of the neural stimulation pattern. In another approach, pulse wave velocity (PWV) or augmentation index (AIx) may be measured, by ultrasonic or pressure sensors respectively, to modulate the timing and extent of the neural stimulation pattern. In another embodiment, the oxygen content of blood may be used as a feedback mechanism to modulate the emulated neurosensory signal. In yet another approach, an EKG signal may be used to identify ST depression as a reflection of myocardial ischemia. This measure may be used to modulate the emulated neurosensory signal. In some cases, stimulation activity can occur without regard to the cardiac cycle (e.g. constant stimulation). During initial system configuration, non-invasive cardiovascular diagnostic devices (e.g. Doppler ultrasound velocimeter, tonometer, plethysmograph, sphygmomanometer) may be used to calibrate the emulated neurosensory signal for best therapeutic effect. In the case for which a multi-electrode nerve cuff is used for afferent nerve stimulation, these non-invasive diagnostic devices may be used to select which electrode(s) to stimulate within the nerve cuff in order to achieve maximum effect.

The third construct relates to the nerves targeted for electronic stimulation and those targeted for feedback sensing. Thus, this construct can include two major subsystems including the stimulation subsystem and the sensory feedback subsystem. The stimulation subsystem accomplishes the neural stimulation by an implantable pulse generator generating the emulated neurosensory signal and conveying that signal to an electrode or electrodes through a lead. Anatomical sites for baroreceptors can include the aortic arch and carotid sinus, and the target nerves can include those whose neural connections involve those sites. This can include the VN, ADN, and CSN. The ADN has been located in humans in recent clinical investigations. Since the ADN—which carries neural traffic arising from aortic baroreceptors—is more selective than the VN, the inventor has determined that it can be desirable to stimulate this nerve. This can allow for fewer unwanted side effects of stimulation.

Some embodiments of this disclosure include a nerve cuff designed to match the morphology, size, and location of all the target nerves. In some examples, a nerve cuff can be specifically intended for the ADN. Clinical investigations show that the ADN can have an approximate diameter of between 0.4 and 0.75 millimeters (mm) and can have a generally circular cross sectional area. In addition, surrounding anatomic structures can limit the allowable footprint of the nerve cuff and the proposed design accommodates this. The CSN can have an approximate diameter of 1 mm and has a generally elliptical cross sectional area. The feedback system may involve a sensing cuff on the afferent target nerve or an efferent nerve as the feedback pathway. Some example implementations can utilize zero feedback.

The nerves cuffs and electrodes may be arranged in various topologies. In some example configurations, at least one nerve cuff can be applied to the right CSN and at least one nerve cuff can be applied to the right ADN in the neck. In some example configurations, at least one nerve cuff can be applied to the left CSN and at least one nerve cuff can be applied to the left ADN in the neck. Desirably, the two aforementioned configurations can limit the number of incisions to implant the nerve cuff to one. Also desirably, the sympathetic activity, and the concomitant reduction in blood pressure and heart rate, is reduced to a greater degree than for the case of stimulating only one nerve. In another example configuration, at least one nerve cuff can be applied to the right CSN and another is applied to the left CSN. In another example configuration, at least one nerve cuff can be applied to the right ADN and at least one nerve cuff can be applied to the left ADN. In another example configuration, at least one nerve cuff can be applied to one of the left or right ADN or CSN. In another example configuration, a single nerve cuff can be applied to the left or right CSN or ADN. There may also be single or multiple electrodes within each nerve cuff. A multiple electrode stimulation nerve cuff configuration can allow the system to compensate for potential cuff migration as well as nerve fatigue.

FIG. 1 illustrates a system 100 configured to acquire and record a signal representative of nerve traffic acquired from a patient 101 equipped with an electromechanical counter-pulsation device 102. In the embodiment shown in FIG. 1, an electrode 104 is shown in contact with a target nerve 106. The electrode 104 can be an electrode cuff, such as a multiple-electrode cuff. In some embodiments, the electrode 104 is proximate to, but not in contact with, the target nerve 106 (e.g., an electric field sensing electrode). The target nerve 106 can be an afferent nerve that carries sensory information from baroreceptors. In example configurations, the electrode 104 can be configured to sense afferent sensory traffic from baroreceptors along the CSN or the ADN.

The electrode 104 is coupled to an extracorporeal recording system 110 via a lead 108. The recording system 110 is configured to sample and record nerve traffic from the afferent nerve 106 that arises from mechanical compression or stimulation of the aorta or pulmonary artery via the electromechanical counter-pulsation device 102. The recording system 110 includes a memory configured to store the recorded signal 112. As will be described hereinbelow, the recorded signal 112 or a derivative of the recorded signal 112 is subsequently used as an emulated neurosensory signal delivered to an afferent nerve (e.g., CSN or ADN) by an electronic neuromodulation system implanted in the same or different patient 101. By stimulating the afferent nerve using an emulated neurosensory signal, the electronic neuromodulation system accomplishes by electronic neuromodulation techniques what the electromechanical counter-pulsation device 102 accomplishes by electromechanical techniques.

According to some embodiments, the electromechanical counter-pulsation device 102 is configured as an extra-aortic balloon pump counter-pulsation system. Suitable extra-aortic balloon pump counter-pulsation systems include those disclosed in U.S. Pat. Nos. 7,740,575 and 8,777,833, and in US Published Patent Application No. 2004/0097783, which are incorporated herein by reference. In other embodiments, the electromechanical counter-pulsation device 102 is configured as an intra-aortic balloon pump counter-pulsation system. A suitable intra-aortic balloon pump counter-pulsation system is disclosed in US Published Patent Application No. 2004/0097784, which is incorporated herein by reference.

In some embodiments, the recording system 110 is configured to record nerve traffic from two or more afferent nerves. For example, a first electrode and lead can be used to sense nerve traffic along the CSN arising from compression of the aorta or the pulmonary artery or stimulation of their baroreceptors. A second electrode and lead can be used to sense nerve traffic along the ADN arising from compression of the aorta or the pulmonary artery or stimulation of their baroreceptors. The recording system 110 can record the CSN signal and the ADN signal, from which respective emulated neurosensory signals can be produced for use in an electronic neuromodulation system configured to stimulate both the CSN and ADN.

According to various embodiments, the system 100 shown in FIG. 1 can be used to sample and record nerve traffic in response to aortic counter-pulsation for a broad number of different patients. For example, a one-time study of a broad number of patients can produce a broad number of recorded signals 112 in order to capture a full range of potential responses. These recorded signals 112 or signals derived from the recorded signals 112 can be used to produce an emulated neurosensory signal which is stored in an electronic neuromodulation system to be implanted in a patient.

Figure 2A:
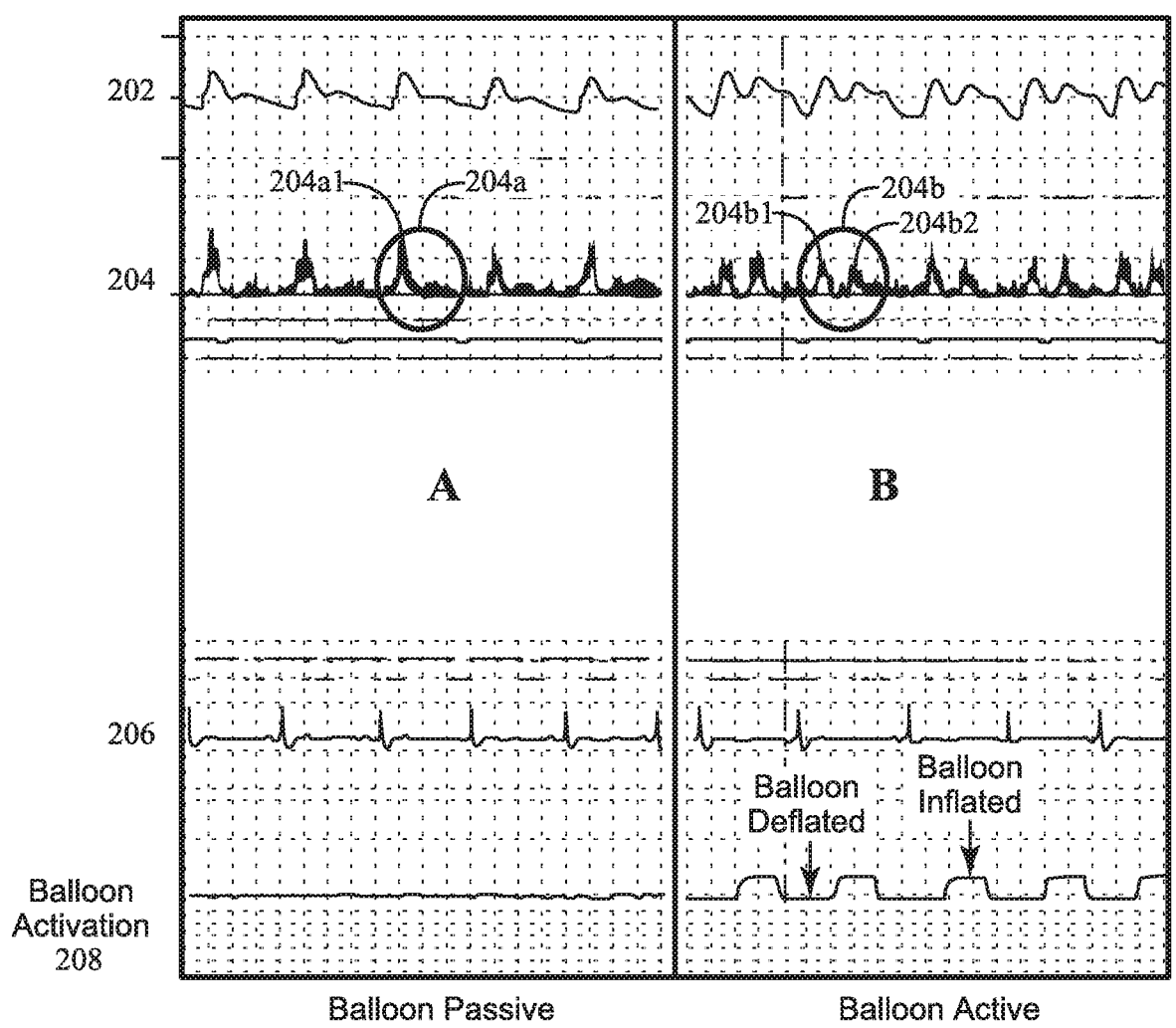
FIG. 2A illustrates various signals associated with intra-aortic balloon pump counter-pulsation applied to a patient's aorta.

FIG. 2A illustrates various signals associated with intra-aortic balloon pump counter-pulsation applied to a patient's aorta. More particularly, the signals shown in FIG. 2A were acquired from a patient equipped with an intra-aortic balloon pump counter-pulsation system. Panel A shows the various signals when the balloon was passive (not inflated). Panel B shows the various signals when the balloon was active (inflated). Signal 202 is a blood pressure signal, signal 204 is a baroreceptor response signal recorded directly from the CSN, signal 206 is an electrocardiogram (ECG) signal, and signal 208 is a balloon inflation signal. It is noted that the CSN signal 204 shown in Panel B of FIG. 2A can be recorded by the recording system 110 shown in FIG. 1.

The circled portion 204a of the CSN signal 204 in Panel A shows a single peak 204a1 of the nerve traffic signal which corresponds to peak systole as a result of contraction of the patient's heart. The circled portion 204b of the CSN signal 204 in Panel B shows two peaks 204b1 and 204b2 of the nerve traffic signal. The first peak 204b1 corresponds to the patient's heart contraction at peak systole (which has been modified by unloading of the aorta by counter-pulsation). The second peak 204b2 corresponds to an augmentation in arterial pressure during diastole due to full inflation of the balloon (see signal 208) and the concomitant maximum compression of the aorta. FIG. 2A demonstrates that application of counter-pulsation to the patient's aorta essentially doubles the baroreceptor activity during each cardiac cycle. It is noted that a key pathology in heart failure is a reduction in activity of the baroreceptors and overall reduced signaling to the brain which results in elevated sympathetic outflow and reduction in parasympathetic outflow. The increase in baroreceptor signaling shown in FIG. 2A reverses this pathology.

Figure 2B:
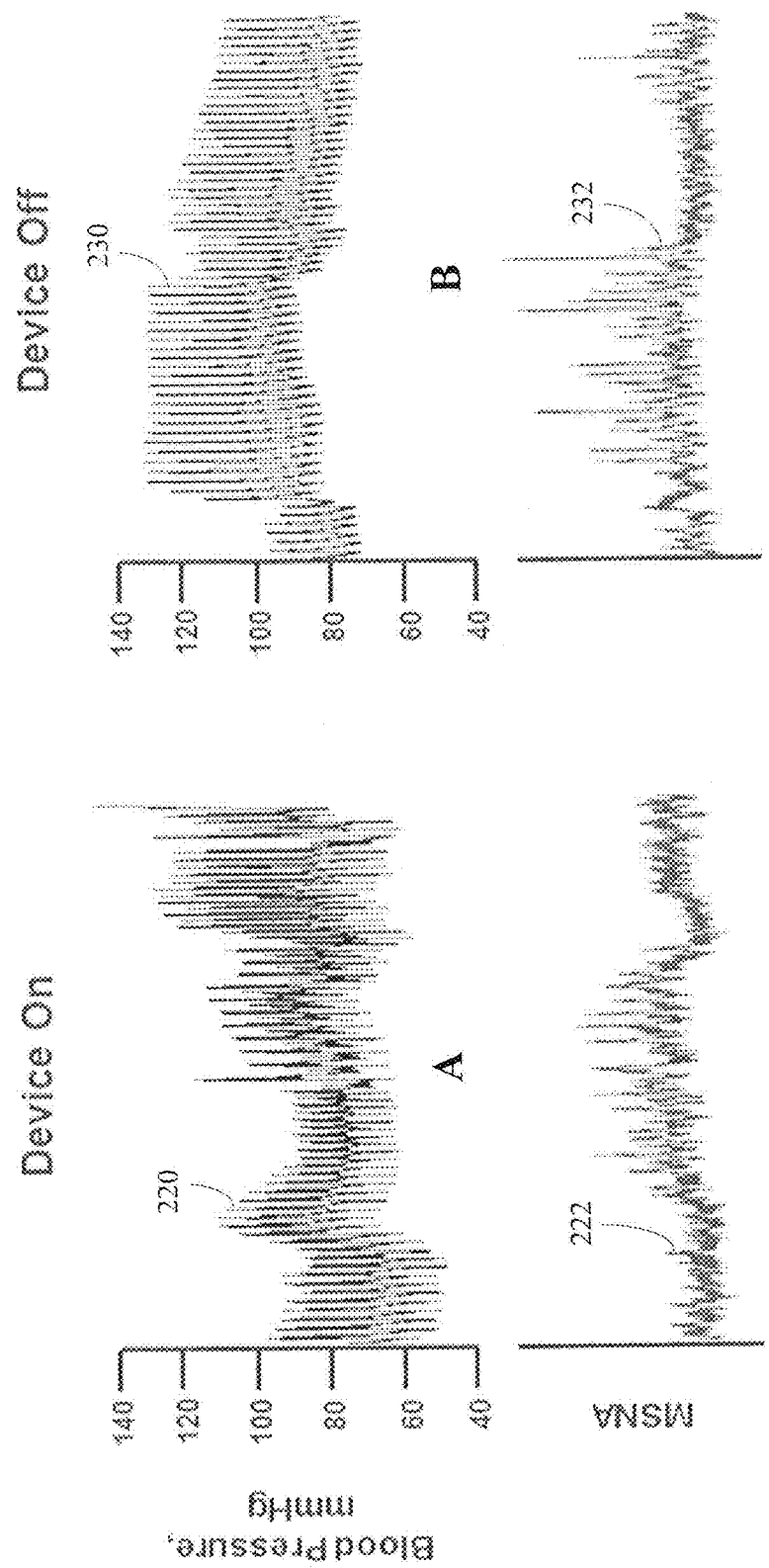
FIG. 2B illustrates various signals associated with extra-aortic balloon pump counter-pulsation applied to a patient's aorta.

FIG. 2B illustrates various signals associated with extra-aortic balloon pump counter-pulsation applied to a patient's aorta. More particularly, the signals shown in FIG. 2B were acquired from a patient equipped with an extra-aortic balloon pump counter-pulsation system. Panel A shows the various signals when the balloon was active (inflated). Panel B shows the various signals when the balloon was inactive (not inflated). Signal 220 is a blood pressure signal with the extra-aortic balloon pump counter-pulsation system ON, and signal 230 is a blood pressure signal with the counter-pulsation system OFF. Signals 220 and 230 shown in FIG. 2B demonstrate a benefit from aortic electromechanical counter-pulsation, in which central blood volume is acutely reduced when the counter-pulsation system is ON.

Signal 222 in Panel A of FIG. 2B is sympathetic efferent nerve traffic that arises from afferent nerve traffic when the extra-aortic balloon pump counter-pulsation system is ON. Signal 232 in Panel B is sympathetic efferent nerve traffic that arises from afferent nerve traffic when the extra-aortic balloon pump counter-pulsation system is OFF. It is noted that signals 222 and 232 are muscle sympathetic nerve activity (MSNA) signals. Signals 222 and 232 shown in FIG. 2B demonstrate a benefit from aortic electromechanical counter-pulsation, in which sympathetic efferent nerve traffic is acutely reduced when the counter-pulsation system is ON.

Figure 3:
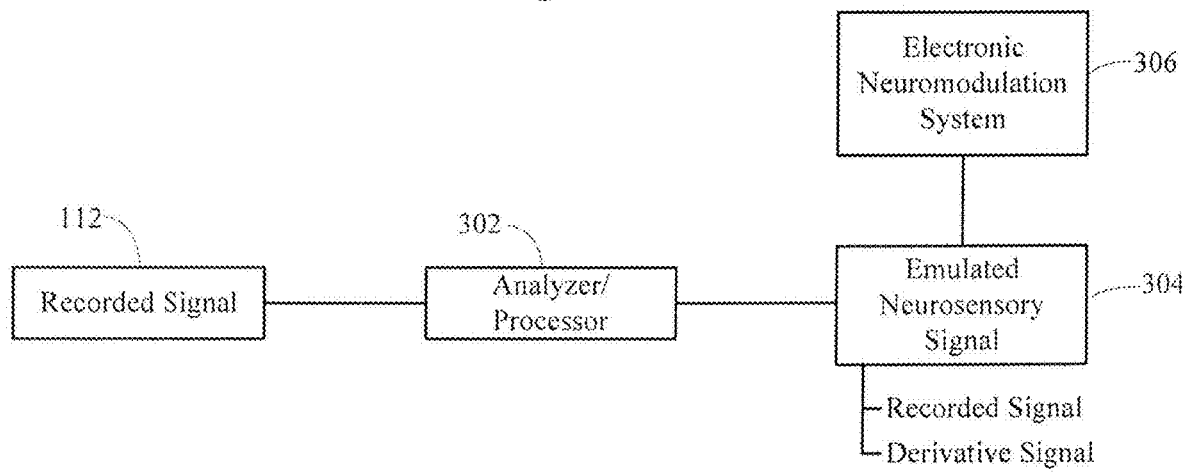
FIG. 3 illustrates a system and process for producing an emulated neurosensory signal from a recorded nerve traffic signal acquired by the recording system shown in FIG. 1 in accordance with various embodiments.

FIG. 3 illustrates a system and process for producing an emulated neurosensory signal from a recorded nerve traffic signal 112 acquired by the recording system 110 shown in FIG. 1. A recorded signal 112 acquired by the system 100 shown in FIG. 1 can be input to an analyzer/processor 302. The analyzer/processor 302 operates on the recorded signal 112 to produce an emulated neurosensory signal 304. In some embodiments, the emulated neurosensory signal 304 is the recorded signal 112 itself or a version of the recorded signal 112 (e.g., an amplitude-scaled version). In other embodiments, the emulated neurosensory signal 304 is a derivative signal resulting from processing of the original recorded signal 112 by the analyzer/processor 302. For example, the recorded signal 112 may be modified (e.g., electronically filtered, amplified, impedance matched, mathematically transformed, etc.) or left unmodified by the analyzer/processor 302 The emulated neurosensory signal 304 can be stored in a memory of an electronic neuromodulation system 306 to be implanted in a patient.

In some embodiments, the analyzer/processor 302 is configured to perform a mathematical transformation or parametric spectral analysis on the recorded signal 112. For example, and without limitation, a Fourier Transform (e.g. Fast Fourier Transform), Burg Transform, or Welch Transform maybe applied to the original recorded signal 112 and the predominant harmonic frequencies of the recorded signal 112 can be identified. The analyzer/processor 302 can perform an inverse transform operation to construct a new time domain signal using the dominant frequency components of the recorded signal 112. This constructed time domain signal can be output by the analyzer/processor 302 as the emulated neurosensory signal 304 to be used in the electronic neuromodulation system 306 to impress the emulated neurosensory signal 304 onto an afferent nerve.

According to some embodiments, prior to being conveyed to the electronic neuromodulation system 306 to be implanted in a patient, the emulated neurosensory signal 304 may be modulated by a physiological or external feedback signal or another parameter of the patient in order to modify the emulated neurosensory signal 304 and optimize the physiological outcome. Illustratively, the mechanically induced counter-pulsation recorded signal 112 may have been recorded for a patient with a heart rate of 70 beats per minute. For a patient with a heart rate of 100 beats per minute, that same signal 112 may be up converted (via frequency shifting, time stretching, or similar algorithm) to a higher fundamental frequency to match the patient's now higher heart rate.

In another illustrative example, the original recorded signal 112 will be synchronized with the patient's cardiac cycle because the mechanical counter-pulsation is so synchronized. The recorded signal 112, when applied to a new patient, will need to be synchronized to that patient's cardiac cycle. So, the timing, frequency content, morphology, amplitude or other signal characteristic of the emulated neurosensory signal 304 may be modulated or matched to a new patient's physiology. The emulated neurosensory signal 304 may also be timed or matched to the original patient's physiology as that physiology varies in the normal course of events (e.g. heart rate increase with exercise). In some embodiments, nerve traffic from both afferent and efferent nerves may be measured simultaneously to ensure that the emulated neurosensory signal 304 produces the optimal efferent neural traffic for the treatment of heart failure, kidney disease, or vascular disease.

Figure 4:
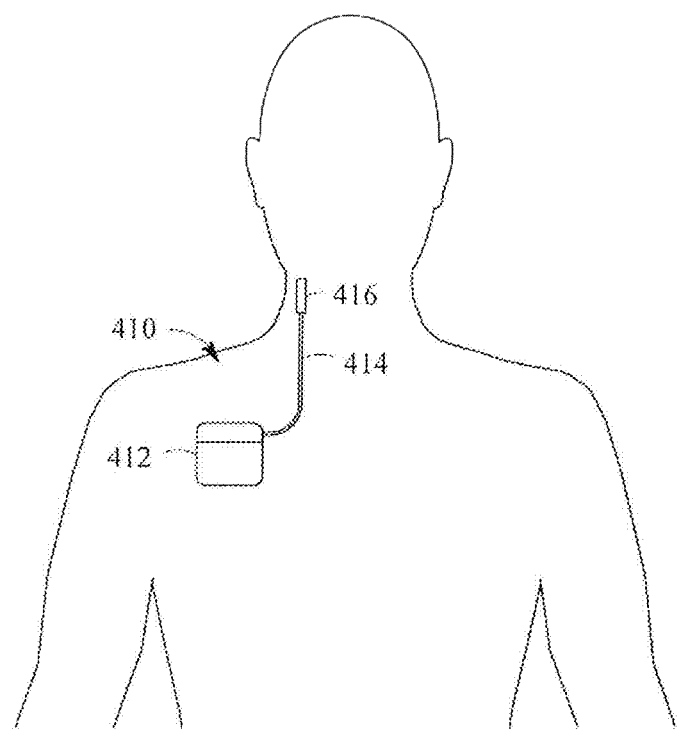
FIG. 4 illustrates an embodiment of an electronic neuromodulation system configured to electrically stimulate an afferent nerve using an emulated neurosensory signal discussed with reference to FIG. 3.
Figure 5:
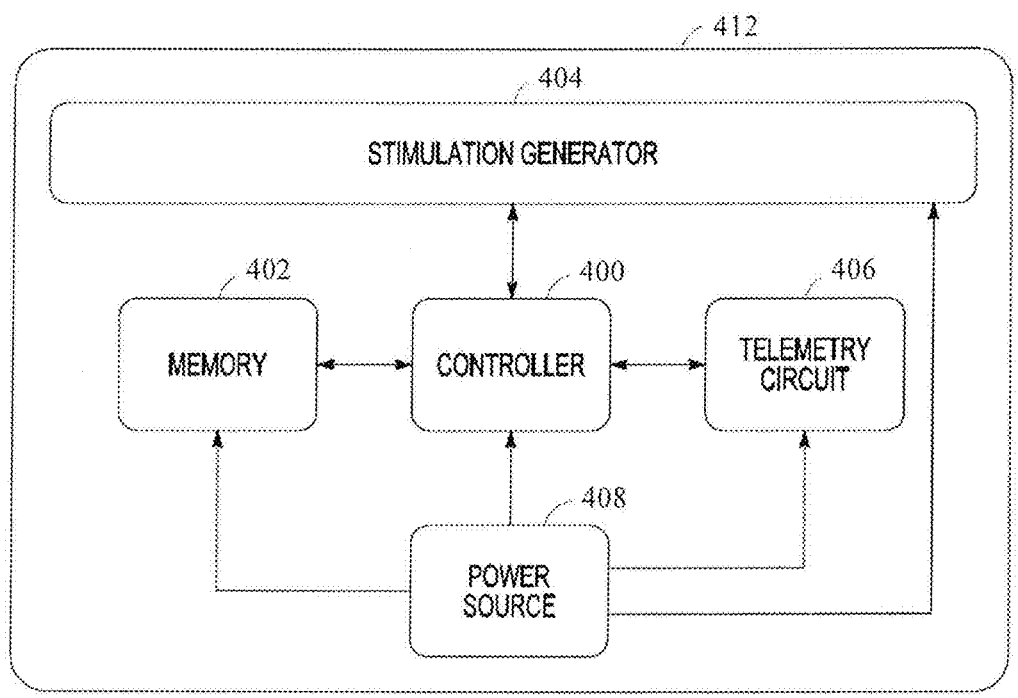
FIG. 5 is a diagram illustrating a representative implantable pulse generator that may be used to implement various aspects of this disclosure.

FIG. 4 illustrates an embodiment of an electronic neuromodulation system 410 configured to electrically stimulate an afferent nerve using an emulated neurosensory signal 304 discussed with reference to FIG. 3. The electronic neuromodulation system 410 shown in FIG. 4 includes an implantable pulse generator 412, a lead 414, and one or more electrodes 416. A representative IPG 412 is depicted in FIG. 5. In the embodiment shown in FIG. 4, the electronic neuromodulation system 410 can include an electrode 416 positioned in the patient to be coupled to the CSN, ADN, or other nerve that carries sensory information from baroreceptors. According to one embodiment, the electrode 416 (and any other electrode in any system disclosed or contemplated herein) can include an electrode cuff. In one example, the electrode cuff can include a bipolar electrode cuff 416 having two electrodes. In another example, the electrode cuff can include a tripolar electrode cuff 416 having three electrodes. Alternatively, the electrode cuff 416 can have four or more electrodes. In a further alternative, the electrode 416 can be a single electrode. In yet further alternative implementations, the electrode 416 can be one, two, three, or more electrodes. In addition to a cuff configuration, in alternative implementations, the electrode 416 can also have other configurations, such as a helical electrode, a patch electrode, a straight electrode, or any other known configuration. It is understood that the lead 414 has an equivalent number of conductors (not shown) depending on the number of electrodes 416. It is further understood that any of these electrode implementations can be incorporated into any system embodiment disclosed or contemplated herein.

FIG. 5 is a diagram illustrating a representative IPG 412 that may be used to implement various aspects of this disclosure. In the example shown in FIG. 5, IPG 412 can include a controller 400, a memory 402, a stimulation generator 404, a telemetry circuitry 406, and a power source 408. The memory 402 can include any volatile or non-volatile media, such as a random access memory (RAM), read only memory (ROM), non-volatile RAM (NVRAM), electrically erasable programmable ROM (EEPROM), flash memory, and the like. The memory 402 can store computer-readable instructions that, when executed by the controller 400, can cause the IPG 412 to perform various functions described in this disclosure. The memory 402 can store, for example, stimulation electrode combinations, therapy programs, and operating instructions. In particular, the memory 402 can store one or more emulated neurosensory signals specific to one or more afferent nerves that carry sensory information from baroreceptors. As was discussed previously, the one or more emulated neurosensory signals stored in the memory 402 allow the electronic neuromodulation system 410 to emulate the function of an electromechanical neuromodulation system (e.g., an intra- or extra-balloon pump counter-pulsation system).

The stimulation generator 404, under the control of the controller 400, can generate emulated neurosensory signals for delivery to the patient via an electrode or selected combinations of electrodes. For example, the stimulation generator 404 can generate the emulated neurosensory signals stored in the memory 402 for delivery to an afferent nerve that carries sensor information from baroreceptors. The power source 408 can deliver operating power to the various components of the IPG 412. The power source 408 can include a rechargeable or non-rechargeable battery and a power generation circuit to produce the operating power. The telemetry circuit 406 can support wireless communication between the IPG 412 and an external programmer (not shown). The telemetry circuit 406 can accomplish communication by various techniques including, but not limited to, proximal inductive interaction, ultrasonic, and radiofrequency (RF) communication techniques. The controller 400 can receive, via the telemetry circuit 406, one or more emulated neurosensory signals from the external programmer for storage in the memory 202, in addition to other parameters.

Figure 6:
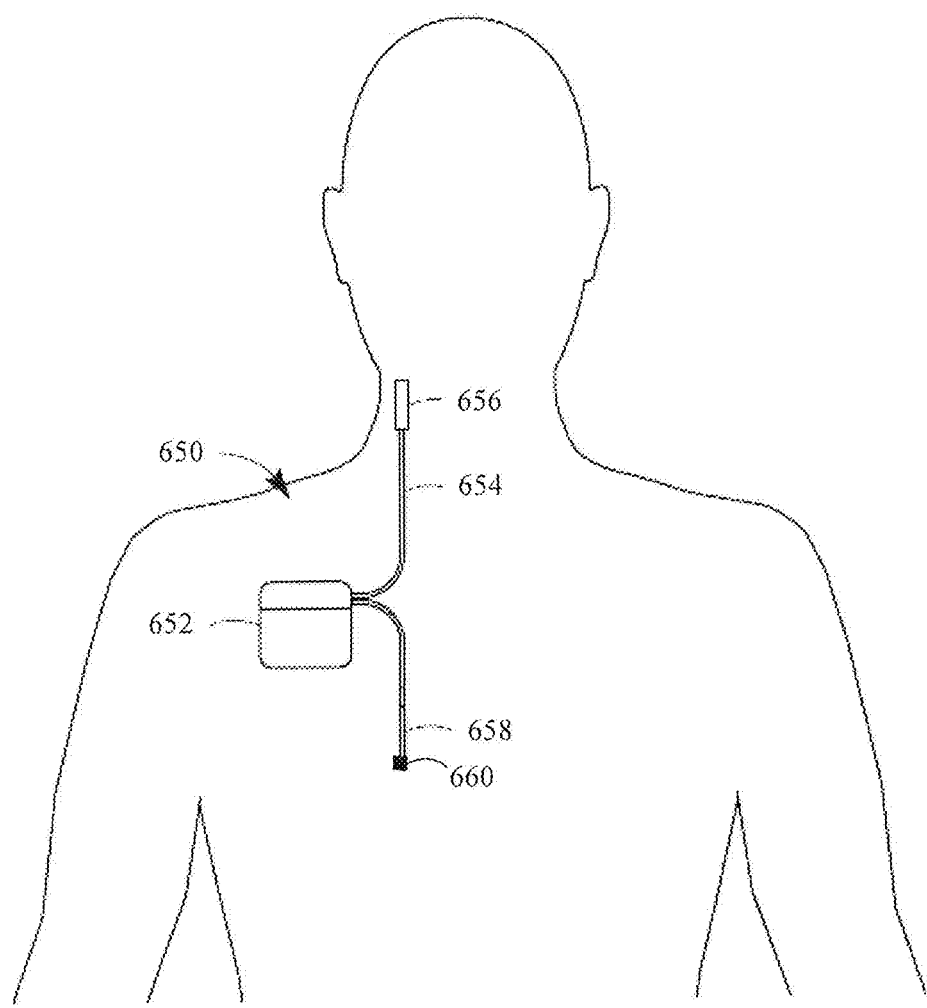
FIG. 6 depicts another embodiment of an electronic neuromodulation system for delivering an emulated neurosensory signal to an afferent nerve in accordance with various embodiments.

FIG. 6 depicts another embodiment of an electronic neuromodulation system 650 for delivering an emulated neurosensory signal to the CSN, ADN, or other nerve that carries sensory information from baroreceptors. In this implementation, the electronic neuromodulation system 650 has not only an implanted IPG 652, a lead 654, and one or more electrodes 656, but also a sensing lead 658 (also referred to as a "sense" or "detection" lead). It is understood that the other components (the IPG 652, lead 654, and electrode 656) can operate in the same fashion or a similar fashion as the corresponding components in the system 410 described above, except as set forth herein. In some examples, electronic neuromodulation system 650 can target one or both of the CSN and the ADN.

The sensing lead 658 is disposed or positioned such that it is adjacent to or in contact with the patient's heart (not shown). In some embodiments, the sensing lead 658 senses an EGM signal, while in other embodiments the sensing lead 658 senses an ECG signal. Alternatively, the sensing lead 658 can be positioned anywhere in or on the patient's body such that the lead 658 can sense electrical heart activity. The sensing lead 658 can be positioned to detect heart signals according to any configuration or method of any known sensing lead. Alternatively, any system embodiment disclosed or contemplated herein can have one or more sensing electrodes without a sensing lead. For example, any system embodiment can have one or more sensing electrodes positioned in the IPG 652 (such as in the header (not shown) of the IPG 652). In a further alternative, the sensing electrodes can be positioned in any known location that can allow for sensing as disclosed herein. In yet another alternative, any system embodiment disclosed herein can have a combination of one or more sensing electrodes at the stimulation site and one or more electrodes positioned in the IPG 652.

In accordance with other embodiments, the sensing lead 658 is configured as a lead coupled to a physiologic sensor 660. In some embodiments, the sensor 660 is configured to sense heart sounds, blood pressure, blood flow or other physiologic signal indicative of cardiac activity. For example, the sensor 660 can include one or more of an ultrasound Doppler sensor (to measure coronary artery or aorta flow), an optical sensor, an acoustic sensor (to detect aortic valve closure), a pulse oximeter (to measure oxygen saturation of blood hemoglobin), or an implantable blood pressure sensor.

The sensing lead 658, alone or in combination with sensor 660, allows for synchronization of the system 650 with a patient's cardiac activity. More specifically, the sensing lead 658 detects one or more signals of the heart and transmits that information to the controller in the IPG 652, which is configured to synchronize the transmission of electrical signals to the electrode 656 to be in desired synchronization with the patient's cardiac activity. In one implementation, the sensing lead 658 is an ECG sense lead, an intracardiac EGM sense lead, an epicardial sense lead, an endocardial sense lead, or a subcutaneous sense lead. Alternatively, and as discussed above, the system 650 can detect the patient's cardiac activity via the sensor 660 configured to detect heart sounds, blood pressure, blood flow or oxygen saturation, for example. In a further alternative implementation, the system 650 can detect the respiration rate and perform some calculation (such as, for example, multiplying the respiration rate by some factor) and thereby approximate the heart rate. While respiration rate is asynchronous to the intrinsic heart rate, the respiration rate is still associated with the patient's physiology and would vary based on metabolic demand. It is understood that any of these heart signal detection components can be incorporated into any of the embodiments disclosed or contemplated herein.

Figure 7:
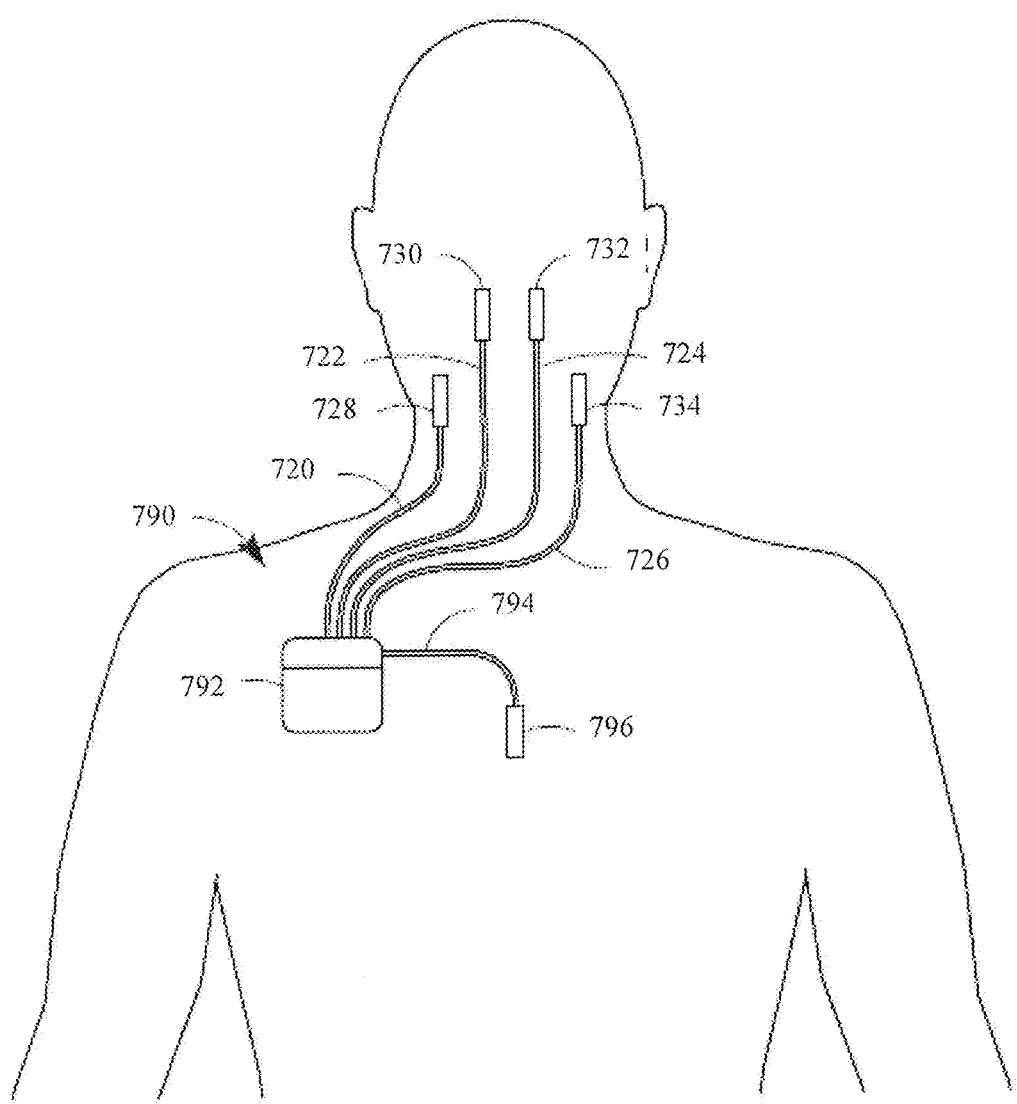
FIG. 7 depicts an embodiment of an electronic neuromodulation system for delivering emulated neurosensory signals to two or more afferent nerves in accordance with various embodiments.

FIG. 7 shows another embodiment of an electronic neuromodulation system 790 for delivering emulated neurosensory signals to two or more of the CSN, ADN, or other nerve that carries sensory information from baroreceptors. The electronic neuromodulation system 790 shown in FIG. 7 includes an IPG 792 coupled to a number of leads 720, 722, 724, and 726 each having one or more respective electrode (s) 728, 730, 732, and 734. These leads and electrodes can be configured to provide electrical stimulation to one or more of a left CSN, left ADN, right CSN, and right ADN. An emulated neurosensory signal specific to one of the left CSN, left ADN, right CSN, and right ADN is stored in a memory of the IPG 792. Although shown having four sets of leads and electrodes in FIG. 7, the electronic neuromodulation system 790 can include as few as two sets of leads and electrodes. The two sets of leads and electrodes can be used to stimulate any combination of the left CSN, left ADN, right CSN, and right ADN.

The IPG 792 is also coupled to a sensing lead 794 which, in some embodiments, is coupled to a sensor 796. The sensing lead 794 and sensor 796 can be configured in a manner similar to the sensing lead 658 and the sensor 660 shown in FIG. 6. The sensing lead 794, alone or in combination with the sensor 796, allows for the synchronized transmission of emulated neurosensory signals to two or more target nerves in synchronization with the patient's cardiac activity (e.g., stimulation during diastole).

According to some embodiments, one of the leads and electrodes shown in FIG. 7 can be coupled to an efferent nerve. This lead and electrode can be used to sense efferent nerve traffic which may be used as a feedback signal by the IPG 792. For example, the IPG 792 can modify the emulated neurosensory signals generated by the IPG 792 in response to the sensed efferent nerve traffic. Additionally, the IPG 792 can further modify the emulated neurosensory signals using one or more physiologic signals acquired by the sensing lead 794, alone or in combination with the sensor 796.

FIG. 8 illustrates a system and method for adjusting and calibrating an electronic neuromodulation system in accordance with various embodiments. The electronic neuromodulation system 801 shown in FIG. 8 includes an IPG 802 coupled to first nerve stimulation lead 804 and second nerve stimulation lead 806. It is understood that each of the nerve stimulation leads 804 and 806 includes one or more electrodes. The first and second nerve stimulation leads 804 and 806 can be coupled to any combination of the left CSN, left ADN, right CSN, and right ADN. In some embodiments, the electronic neuromodulation system 801 includes a single nerve stimulation lead 804 coupled to one of the target nerves.

The IPG 802 is communicatively coupled to an external programmer 810. In the embodiment shown in FIG. 8, the system 800 includes a non-invasive bio-signal monitor 808 coupled to the patient 803 and the programmer 810. According to various embodiments, the non-invasive bio-signal monitor 808 can include a tonometer, Doppler ultrasound, pulse oximeter, sphygmomanometer, or plethysmography sensor, for example. Feedback from the non-invasive bio-signal monitor 808 is used by software of the programmer 810 to adjust and calibrate the electronic neuromodulation system 801. For example, the bio-signal monitor signal can be used to calibrate and modulate emulated neurosensory signals with respect to frequency content, duty cycle, timing, and amplitude.

FIG. 9 illustrates a system and method for adjusting and calibrating an electronic neuromodulation system in real-time in accordance with various embodiments. The electronic neuromodulation system 901 shown in FIG. 9 includes an IPG 902 coupled to first nerve stimulation lead 904 and second nerve stimulation lead 906. It is understood that each of the nerve stimulation leads 904 and 906 includes one or more electrodes. The first and second nerve stimulation leads 904 and 906 can be coupled to any combination of the left CSN, left ADN, right CSN, and right ADN. In some embodiments, the electronic neuromodulation system 901 includes a single nerve stimulation lead 904 coupled to one of the target nerves.

The IPG 902 is communicatively coupled to an external programmer 910. In the embodiment shown in FIG. 9, the system 900 includes an implantable bio-signal monitor 908 coupled to the patient 903 and the IPG 902. According to various embodiments, the implantable bio-signal monitor 908 can include any of the previously mentioned sensors (e.g., ultrasonic, EGM, pressure, acoustic), for example. Real-time feedback from the implantable bio-signal monitor 908 is used by the IPG 902 to adjust and calibrate the electronic neuromodulation system 901. For example, the bio-signal monitor signal can be used to calibrate and modulate emulated neurosensory signals with respect to frequency content, duty cycle, timing, and amplitude.

By way of example, an emulated neurosensory signal can be modified by the electronic neuromodulation system (or the programmer) to accommodate the changing heart rate of the patient. In accordance with embodiments in which the emulated neurosensory signal is a recording of afferent nerve traffic, the emulated neurosensory signal can be delivered (e.g., "played back") at a different rate to accommodate the patient's heart rate (e.g., faster or slower than the original recorded signal). In accordance with embodiments in which the emulated neurosensory signal is a signal derived from a recording of afferent nerve traffic, a Phase Vocoder method or a Pitch Synchronized Overlap and Add (PSOLA) method can be used to modify the emulated neurosensory signal.

According to a representative Phase Vocoder method, a short-time Fourier Transform (STFT) is used to convert the recorded afferent nerve traffic signal into a time-frequency representation. The amplitudes or phases of specific frequency components of the time-frequency representation can be modified to adapt the emulated neurosensory signal to a patient's current heart rate. The time-frequency representation is resampled in the frequency domain, and then inverse transformed back to the time domain as the modified emulated neurosensory signal.

According to a representative PSOLA method, the recorded afferent nerve traffic signal is divided into small overlapping segments. The rate of the emulated neurosensory signal can be changed by moving the segments of the recorded afferent nerve traffic signal apart (to decrease the rate) or closer together (to increase the rate). The duration of the emulated neurosensory signal can be changed by repeating the segments of the recorded afferent nerve traffic signal multiple times (to increase the duration) or eliminating some of the segments (to decrease the duration). The segments are then combined using the overlap add technique to produce the modified emulated neurosensory signal.

The recorded (with concomitant counter-pulsation) afferent neural signal in the CSN that arises from aortic (and other) baroreceptors contains a large number of frequency components. A simplified mathematical model for the action potential caused by counter-pulsation comprises four components that, together, represent the different categories of signal components that make up the counter-pulsation caused afferent neural signal.

$$y = A1*\sin(\text{HRact}/\text{HRbas})*(\omega 1*t) + A2*\sin(\text{HRact}/\text{HRbas})*(\omega 1*t - \varphi 1) + A3*\sin(\text{HRact}/\text{HRbas})*(\omega 2*t - \varphi 2) + A4*\sin(\omega 3*t - \varphi 3) \qquad [1]$$

where, HRact=current patient heart rate, HRbas=recorded patient heart rate, $\omega 1$=dominant frequency corresponding to recorded heart rate, $\omega 2$=frequency of harmonics corresponding to recorded heart rate, ω3=frequency of harmonics not corresponding to recorded heart rate, φ1=phase of arbitrary frequency component corresponding to second term above, φ2=phase of arbitrary frequency component corresponding to third term above, φ3=phase of arbitrary frequency component corresponding to fourth term above, and A1-A4=recorded afferent signal amplitude for each term above.

The first term in Equation [1] above represents the in-phase action potential signal components synchronized with the heart rate that produce a physiological effect. The second term represents the phase delayed, heart rate synchronized signal components that produce a physiological effect. The third term represents the heart rate synchronized signal components that produce no physiological effect. The last term represents the heart rate independent signal components that produce no physiological effect. Each term, therefore, represents multiple signal components.

The original (recorded) signal may be modified (e.g. amplified, attenuated, up-converted, down-converted, time stretched, filtered, etc.) before being conveyed to an electronic neuromodulation system. Illustratively, the original recorded signal may be processed as follows: The original recorded signal may be converted to the frequency domain via Fourier Transform. Once in the frequency domain, the unwanted components can be removed (heart rate independent, physiologically ineffective components). Finally, the processed frequency domain signal may then be inverse transformed back to the time domain to produce an emulated neurosensory signal. The result would, ideally, be the signal depicted below:

$$y = A1 * \sin\left(\frac{HRact}{HRbas}\right) * (\omega 1 * t) + A2 * \sin\left(\frac{HRact}{HRbas}\right) * (\omega 1 * t - \varphi 1)$$

Amplitude scaling would then produce the following signal:

$$y = B1 * \sin\left(\frac{HRact}{HRbas}\right) * (\omega 1 * t) + B2 * \sin\left(\frac{HRact}{HRbas}\right) * (\omega 1 * t - \varphi 1)$$

The aforementioned signal processing may be accomplished by any number of means without departing from the scope of the disclosure. Time or frequency domain filtering may be used to attenuate unwanted frequency components. Digital or analog amplifiers or attenuators may be used without departing from the scope of the disclosure. Conversion from time domain to frequency domain, if needed, may be accomplished using the Direct Fourier Transform (DFT), Fast Fourier Transform (FFT), and/or various parametric transforms without departing from the scope of the disclosure. Further, changing the original recorded signal to accommodate a changing heart rate may be accomplished using any number of time stretching algorithms including but not limited to PSOLA, up/down sampling, etc. without departing from the scope of the disclosure.

Figure 10:
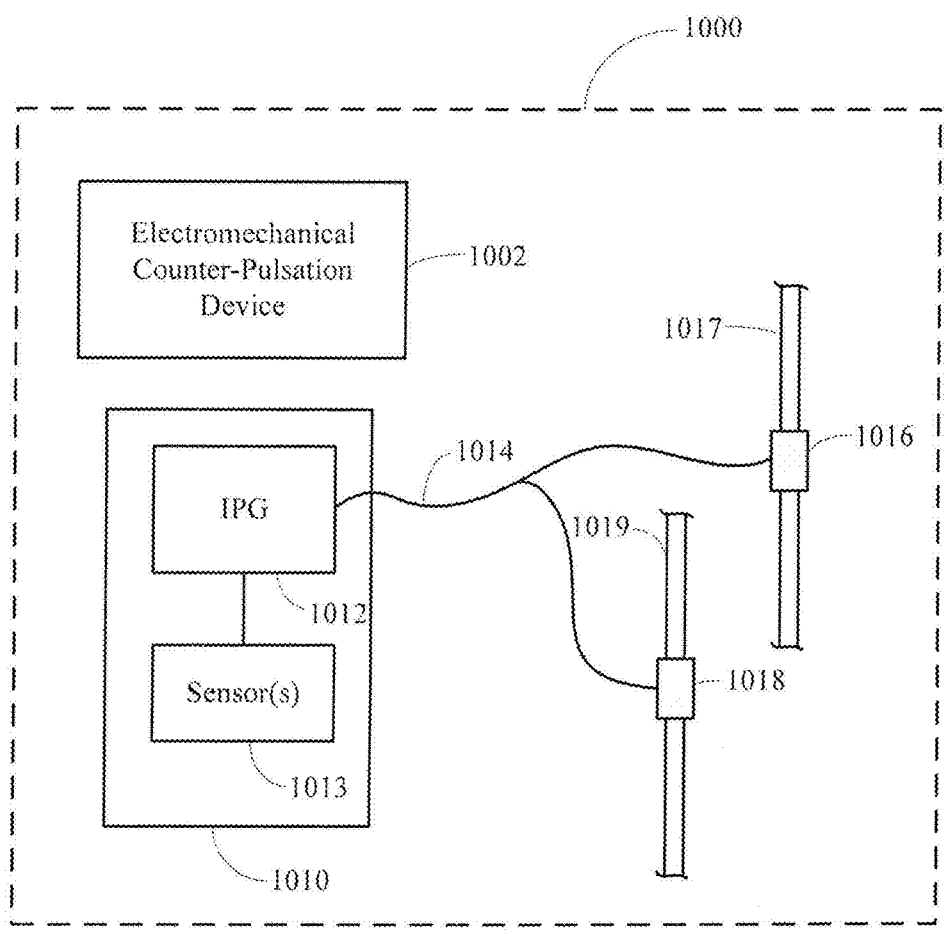
FIG. 10 illustrates a hybrid system which includes an electromechanical counter-pulsation device and an electronic neuromodulation system in accordance with various embodiments.

FIG. 10 illustrates a hybrid system 1000 which includes an electromechanical counter-pulsation device 1002 and an electronic neuromodulation system 1010 in accordance with various embodiments. The electromechanical counter-pulsation device 1002 can be an intra-aortic or an extra-aortic balloon pump counter-pulsation system of a type previously described. The electronic neuromodulation system 1010 can be of a type previously described. For purposes of illustration, the neuromodulation system 1010 of the hybrid system 1000 includes an IPG 1012 coupled to one or more physiologic sensors 1013 and a lead 1014. The lead 1014 is coupled to electrode 1016 and electrode 1018. Illustratively, the electrodes 1016 and 1018 can be coupled to any combination of the left CSN, left ADN, right CSN, and right ADN. In some embodiments, the lead 1014 is coupled to a single electrode 1016 which is coupled to one of the target nerves. The electrodes 1016 and 1018 are configured for both sensing neural signals from and applying electrical stimulation to afferent nerves 1017 and 1019.

Because a patient is equipped with both the electromechanical counter-pulsation device 1002 and the electronic neuromodulation system 1010, the nerve traffic signals needed to produce the emulated neurosensory signals can be obtained directly from the patient. The IPG 1012 can record the nerve traffic signals and communicate the signals to an external programmer. The programmer can analyze and process the nerve traffic signals in a manner previously discussed (see, e.g., FIG. 3) to generate one or more emulated neurosensory signals. The programmer can transmit the emulated neurosensory signals to the IPG 1012 for storage in a memory of the IPG 1012. In some embodiments, the emulated neurosensory signals can be produced using nerve traffic signals acquired from other patients in a manner previously discussed.

The hybrid system 1000 can be configured to provide for three modes of operation, each of which is synchronized to the patient's cardiac activity (e.g., active during diastole). The different modes of operation can be selected by a processor of the IPG 1012 or a processor of the electromechanical counter-pulsation device 1002. Mode One is the lowest level of functionality and involves neuromodulation of one or more afferent nerves using one or more emulated neurosensory signals in a manner previously discussed. In Mode One, the electromechanical counter-pulsation device 1002 is in an inactive state (OFF). Mode One reduces device-induced stress on the aorta and reduces any deleterious effects or pathological changes.

Mode Two turns ON the electromechanical counter-pulsation device 1002 and turns OFF the electronic neuromodulation system 1010. The electromechanical counter-pulsation device 1002 operates in synchrony with the patient's cardiac activity as previously described. Mode Two is typically invoked when the patient requires more cardiovascular support (e.g., upon physical exertion or dyspnea) than for the Mode One. Mode Two reduces electronic neurostimulation-induced stress on the nerves and reduces any deleterious effects on or pathological changes to the nerves.

Mode Three periodically switches between Mode One and Mode Two. It is well known that persistent hypertension may cause resetting of arterial baroreceptors, rendering them less sensitive to blood pressure. Periodic use of Mode One will allow the baroreceptors to re-sensitize, thereby rendering electromechanical counter-pulsation more effective. Mode Three reduces device-induced stress on the aorta and nerves and reduces any deleterious effects on or pathological changes to either the aorta, pulmonary artery, or afferent nerve.

FIGS. 11A-11C illustrate a multi-electrode nerve cuff in accordance with various embodiments. The nerve cuff 1100 shown in FIGS. 11A-11C includes a body 1104 and a cavity 1105 dimensioned to receive a nerve 1102, such as a CSN or ADN. Extending from the body 1104 are tabs 1106a and 1106b that can be manipulated to open and close the nerve cuff 1100. The tabs 1106a and 1106b are separable at the tip to allow for tool insertion. A shoulder 1107 extends from the body 1104 and is configured to receive a distal end of a lead body 1110. The shoulder 1107 maintains the lead body 1110 in an orientation that is parallel to the nerve 1102 and offset from the body 1104. Suture grooves 1108 are provided on the body 1104.

The cavity 1105 is contoured to match the shape of the nerve 1102. For example, the cavity 1105 can have a generally elliptical shape (e.g., an elliptical cross-section) to match the elliptical shape of the nerve 1102, such as a CSN. In some implementations, the cavity 1105 can have a generally circular shape (e.g., a circular cross-section) to match the circular shape of the nerve 1102, such as an ADN. According to some embodiments, the cavity 1105 has dimensions of about 1.5 mm×2.5 mm. Disposed on the wall of the cavity 1105 are electrodes 1112*a*, 1112*b*, and 1112*c*. Although three electrodes 1112 are shown in FIG. 11C, it is understood that more or fewer electrodes can be disposed on the wall of the cavity 1105.

Figure 12A:
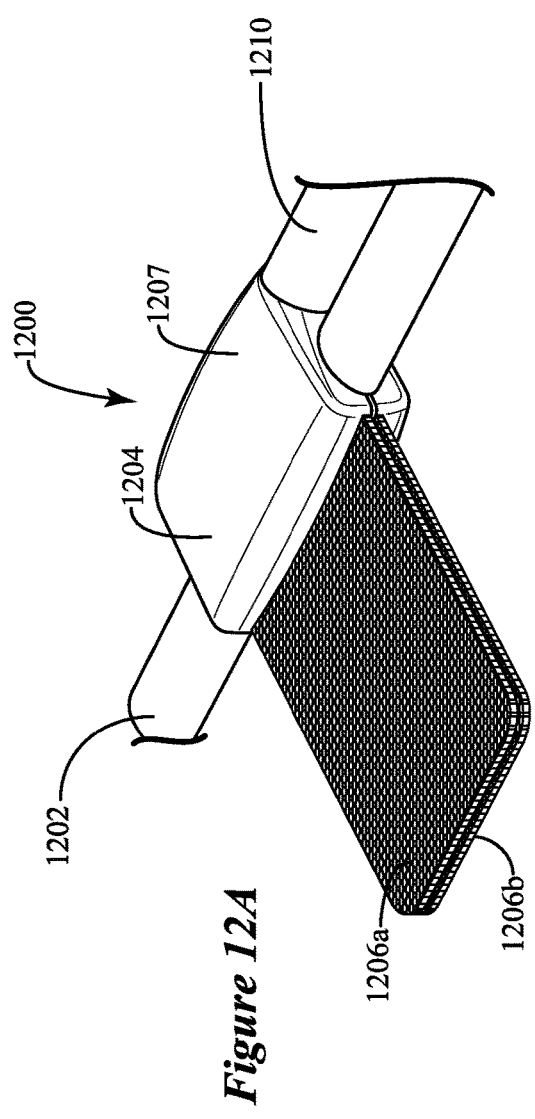
FIGS. 12A-12C illustrate a multi-electrode nerve cuff in accordance with various embodiments.
Figure 12B:
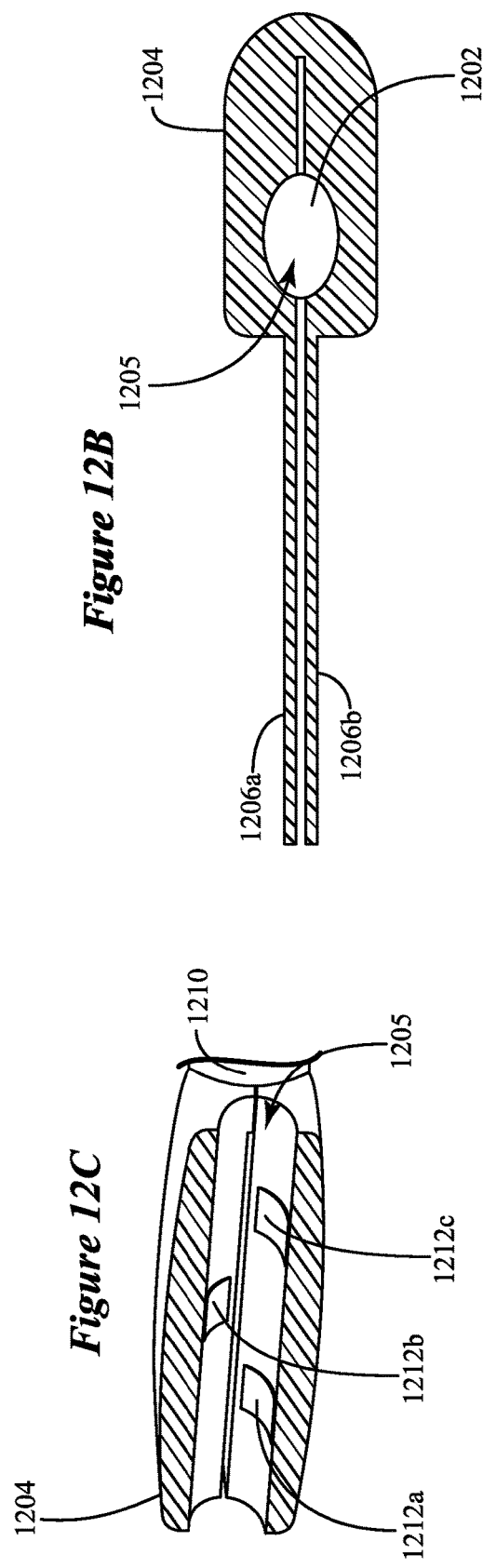
Figure 12C:
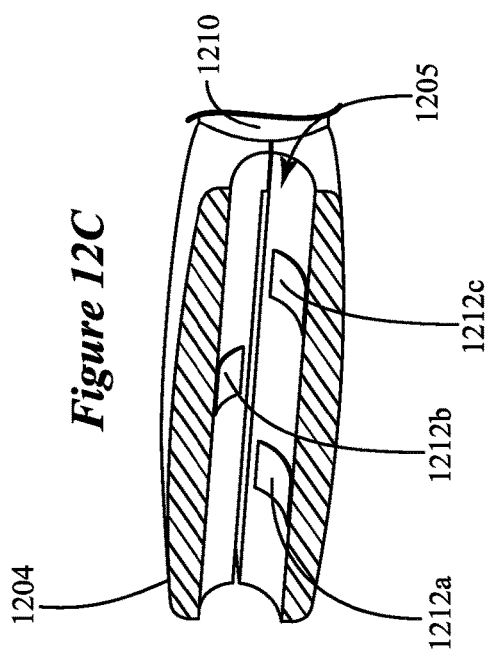

FIGS. 12A-12C illustrate a multi-electrode nerve cuff in accordance with various embodiments. The nerve cuff 1200 shown in FIGS. 12A-12C includes a body 1204 and a cavity 1205 dimensioned to receive a nerve 1202, such as a CSN or ADN. Extending from the body 1204 are tabs 1206*a* and 1206*b* that can be manipulated to open and close the nerve cuff 1200. The tabs 1206*a* and 1206*b* can be formed from reinforced silicone and can be sutured together. The tabs 1206*a* and 1206*b* can extend along the entire length of the body 1204. A shoulder 1207 extends from the body 1204 and is configured to receive a distal end of a lead body 1210. The shoulder 1207 maintains the lead body 1210 in an orientation that is parallel to the nerve 1202 and offset from the body 1204.

The cavity 1205 is contoured to match the shape of the nerve 1202. For example, the cavity 1205 can have a generally elliptical shape (e.g., an elliptical cross-section) to match the elliptical shape of the nerve 1202, such as a CSN. In some implementations, the cavity 1205 can have a generally circular shape (e.g., a circular cross-section) to match the circular shape of the nerve 1202, such as an ADN. According to some embodiments, the cavity 1205 has dimensions of about 1.5 mm×2.5 mm. Disposed on the wall of the cavity 1205 are electrodes 1212*a*, 1212*b*, and 1212*c*. Although three electrodes 1212 are shown in FIG. 12C, it is understood that more or fewer electrodes can be disposed on the wall of the cavity 1205. The nerve cuff 1200 shown in FIGS. 12A-12C can be easily secured to the nerve 1202 and sutured. Also, conductor placement of the nerve cuff 1200 minimizes the bending moment on vasculature.

FIGS. 13A-13C illustrate a multi-electrode nerve cuff in accordance with various embodiments. The nerve cuff 1300 shown in FIGS. 13A-13C includes a body 1304 and an open cavity 1305 dimensioned to receive a nerve 1302, such as a CSN or ADN. Extending from the body 1304 are tabs 1306*a* and 1306*b* that can be manipulated to open and close the nerve cuff 1300. The tabs 1306*a* and 1306*b* are buckle-style tabs in the embodiment shown in FIGS. 13A-13C. Tab 1306*a* includes apertures 1309 and tab 1306*b* includes belt members 1311. The nerve cuff 1300 is self-closing and is easily secured to the nerve 1302. Apertures 1309 allow for suturing of the tabs 1306*a* and 1306*b*. A shoulder 1307 extends from the body 1304 and is configured to receive a distal end of a lead body 1310. The shoulder 1307 maintains the lead body 1310 in an orientation that is parallel to the nerve 1302 and offset from the body 1304.

The wall of the open cavity 1305 that encompasses the nerve 1302 is contoured to match the shape of the nerve 1302. For example, the open cavity 1305 that encompasses the nerve 1302 can have a generally elliptical shape (e.g., an elliptical cross-section) to match the elliptical shape of the nerve 1302, such as a CSN. In some implementations, the open cavity 1305 can have a generally circular shape (e.g., a circular cross-section) to match the circular shape of the nerve 1302, such as an ADN. According to some embodiments, the open cavity 1305 has dimensions of about 1.5 mm×2.5 mm. Disposed on the wall of the cavity 1305 proximate the body 1304 are electrodes 1312*a*, 1312*b*, and 1312*c*. Although three electrodes 1312 are shown in FIG. 13C, it is understood that more or fewer electrodes can be disposed on the wall of the cavity 1305. Conductor placement of the nerve cuff 1300 minimizes the bending moment on vasculature.

Figure 14A:
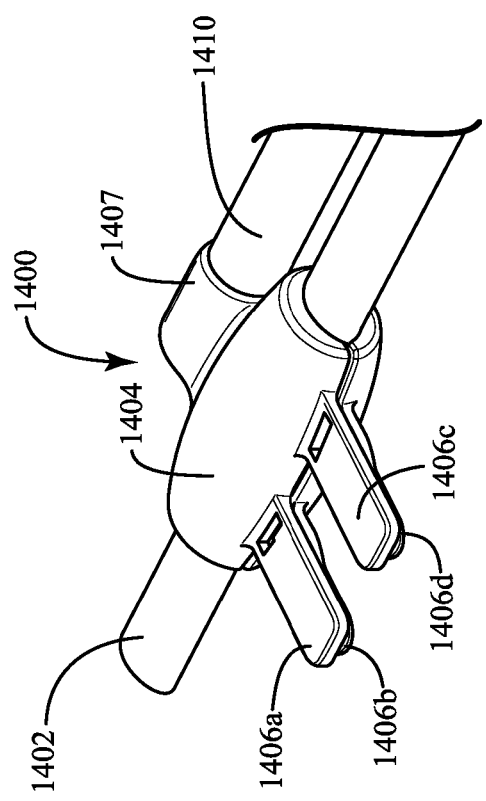
FIGS. 14A-14C illustrate a multi-electrode nerve cuff in accordance with various embodiments.
Figure 14B:
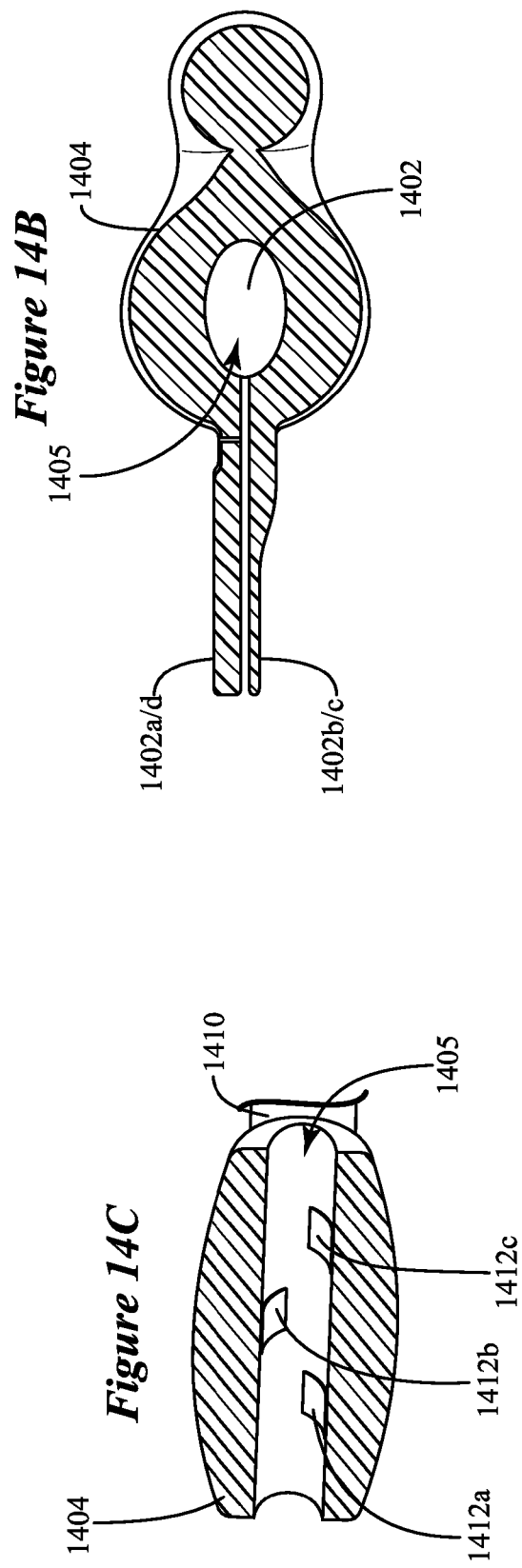
Figure 14C:
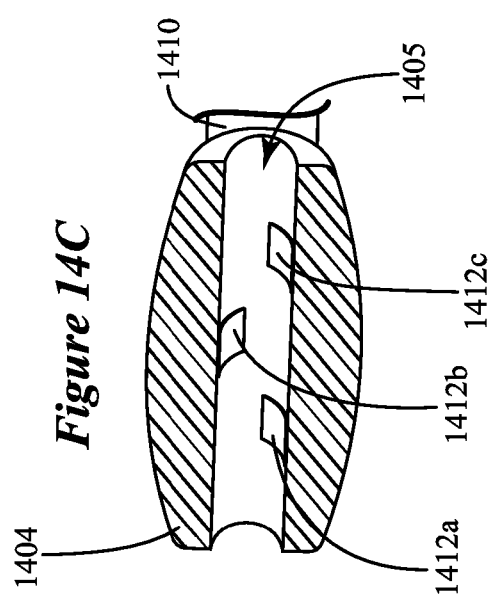

FIGS. 14A-14C illustrate a multi-electrode nerve cuff in accordance with various embodiments. The nerve cuff 1400 shown in FIGS. 14A-14C includes a body 1404 and a cavity 1405 dimensioned to receive a nerve 1402, such as a CSN or ADN. Extending from the body 1404 are first tabs 1406*a/b* and second tabs 1406*c/d* that can be manipulated to open and close the nerve cuff 1400. The first and second tabs 1406*a/b* and 1406*c/d* are buckle-style tabs, and can be sutured. A shoulder 1407 extends from the body 1404 and is configured to receive a distal end of a lead body 1410. The shoulder 1407 maintains the lead body 1410 in an orientation that is parallel to the nerve 1402 and offset from the body 1404.

The cavity 1405 is contoured to match the shape of the nerve 1402. For example, the cavity 1405 can have a generally elliptical shape (e.g., an elliptical cross-section) to match the elliptical shape of the nerve 1402, such as a CSN. In some implementations, the cavity 1405 can have a generally circular shape (e.g., a circular cross-section) to match the circular shape of the nerve 1402, such as an ADN. According to some embodiments, the cavity 1405 has dimensions of about 1.5 mm×2.5 mm. Disposed on the wall of the cavity 1405 are electrodes 1412*a*, 1412*b*, and 1412*c*. Although three electrodes 1412 are shown in FIG. 14C, it is understood that more or fewer electrodes can be disposed on the wall of the cavity 1405.

Figure 15A:
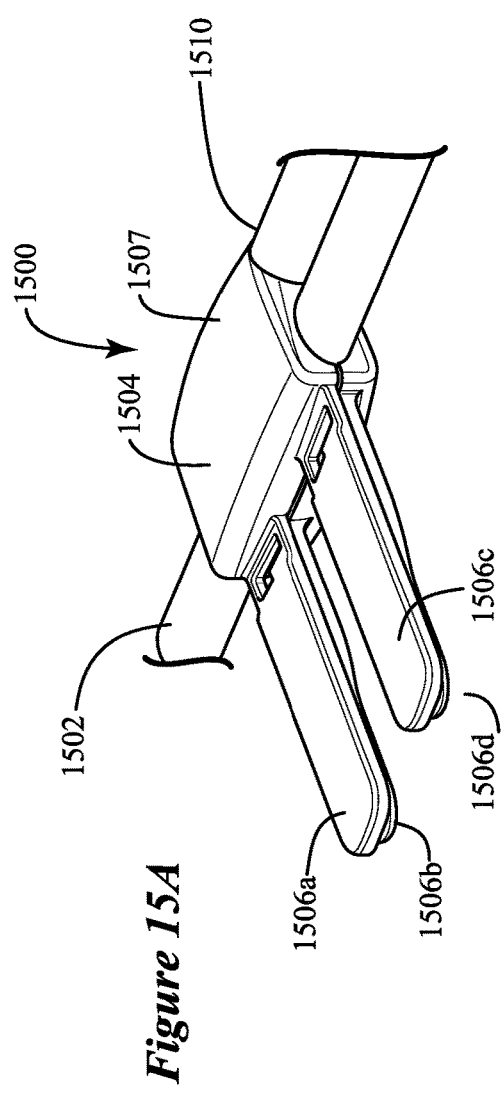
FIGS. 15A-15C illustrate a multi-electrode nerve cuff in accordance with various embodiments.
Figure 15B:
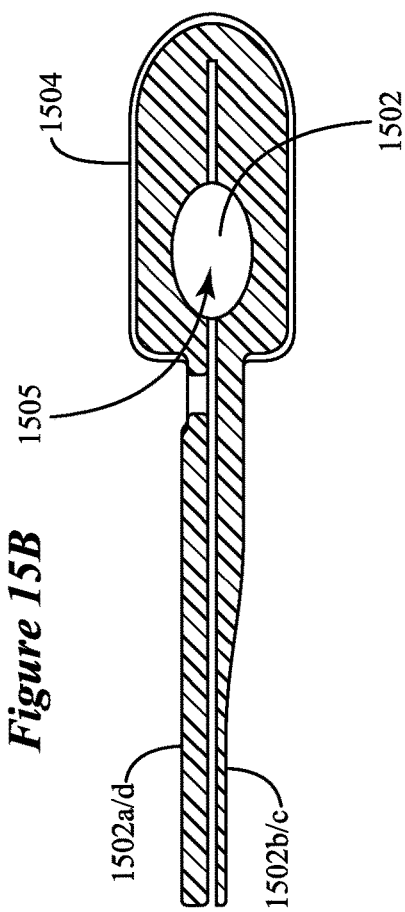
Figure 15C:
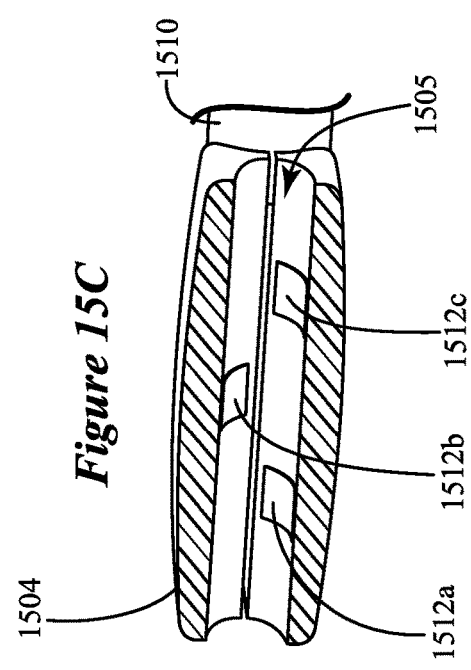

FIGS. 15A-15C illustrate a multi-electrode nerve cuff in accordance with various embodiments. The nerve cuff 1500 shown in FIGS. 15A-15C includes a body 1504 and a cavity 1505 dimensioned to receive a nerve 1502, such as a CSN or ADN. Extending from the body 1504 are first tabs 1506*a/b* and second tabs 1506*c/d* that can be manipulated to open and close the nerve cuff 1500. The first and second tabs 1506*a/b* and 1506*c/d* are buckle-style tabs, and can be sutured. A shoulder 1507 extends from the body 1504 and is configured to receive a distal end of a lead body 1510. The shoulder 1507 maintains the lead body 1510 in an orientation that is parallel to the nerve 1502 and offset from the body 1504.

The cavity 1505 is contoured to match the shape of the nerve 1502. For example, the cavity 1505 can have a generally elliptical shape (e.g., an elliptical cross-section) to match the elliptical shape of the nerve 1502, such as a CSN. In some implementations, the cavity 1505 can have a generally circular shape (e.g., a circular cross-section) to match the circular shape of the nerve 1502, such as an ADN. According to some embodiments, the cavity 1505 has dimensions of about 1.5 mm×2.5 mm. Disposed on the wall of the cavity 1505 are electrodes 1512*a*, 1512*b*, and 1512*c*. Although three electrodes 1512 are shown in FIG. 15C, it is understood that more or fewer electrodes can be disposed on the wall of the cavity 1505. Conductor placement of the nerve cuff 1500 minimizes the bending moment on vasculature.

Figure 16A:
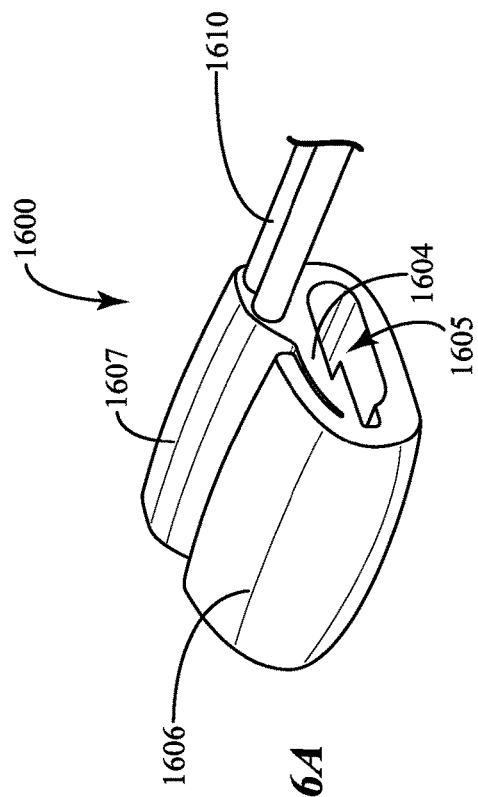
FIGS. 16A-16C illustrate a multi-electrode nerve cuff in accordance with various embodiments.
Figure 16B:
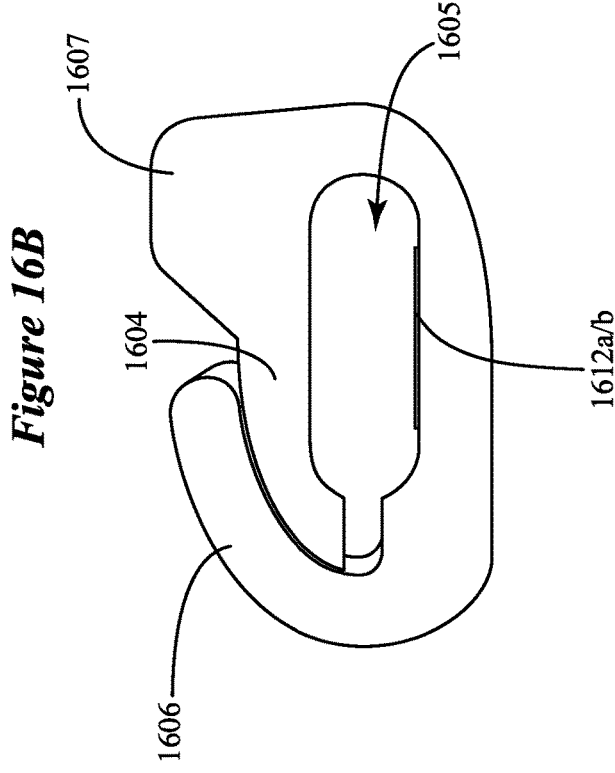
Figure 16C:
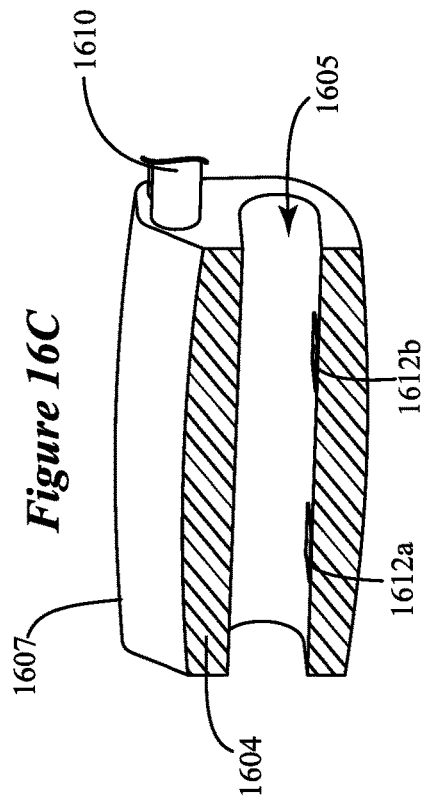

FIGS. 16A-16C illustrate a multi-electrode nerve cuff in accordance with various embodiments. The nerve cuff 1600 shown in FIGS. 16A-16C includes a body 1604 and a flat cavity 1605 dimensioned to receive a nerve 1602, such as a CSN or ADN. According to some embodiments, the flat cavity 1605 has dimensions of about 1.5 mm×4.5 mm. Extending from the body 1604 is a formed tab 1606 configured to wrap around onto the body 1604. The formed tab 1606 can be manipulated to open and close the nerve cuff 1600. The nerve cuff 1600 is self-closing after receiving a nerve in the flat cavity 1605. The nerve cuff 1600 is easily secured to the nerve and may not need sutures. A shoulder 1607 extends from the body 1604 and is configured to receive a distal end of a lead body 1610. The shoulder 1607 maintains the lead body 1610 in an orientation that is parallel to the nerve 1602 and offset from the body 1604. Disposed on the wall of the cavity 1605 are electrodes 1612a and 1612b. Although two electrodes 1612 are shown in FIG. 16C, it is understood that more or fewer electrodes can be disposed on the wall of the cavity 1605.

Systems, devices or methods disclosed herein may include one or more of the features structures, methods, or combination thereof described herein. For example, a device or method may be implemented to include one or more of the features and/or processes above. It is intended that such device or method need not include all of the features and/or processes described herein, but may be implemented to include selected features and/or processes that provide useful structures and/or functionality. Various modifications and additions can be made to the disclosed embodiments discussed above. Accordingly, the scope of the present disclosure should not be limited by the particular embodiments described above, but should be defined only by the claims set forth below and equivalents thereof.

What is claimed is:

1. A system, comprising:
   an implantable electronic neuromodulation system including an implantable pulse generator comprising a controller and a memory, the memory configured to store an emulated neurosensory signal representative of nerve traffic acquired from a patient equipped with an extra-aortic balloon pump counter-pulsation system or an intra-aortic balloon pump counter-pulsation system;
   a lead coupled to the implantable pulse generator; and
   at least one electrode coupled to the lead, wherein the at least one electrode is positionable in contact with or adjacent to at least one nerve that carries sensory information from baroreceptors;
   wherein the controller is configured to stimulate the at least one nerve using the emulated neurosensory signal.

2. The system of claim 1, wherein the at least one electrode is positionable in contact with or adjacent to a carotid sinus nerve.

3. The system of claim 1, wherein the at least one electrode is positionable in contact with or adjacent to an aortic depressor nerve.

4. The system of claim 1, comprising a plurality of electrodes respectively coupled to the lead, wherein the plurality of electrodes are positionable in contact with or adjacent to any combination of a left carotid sinus nerve, a right carotid sinus nerve, a left aortic depressor nerve, and a right aortic depressor nerve.

5. The system of claim 1, wherein the emulated neurosensory signal is representative of traffic along a carotid sinus nerve.

6. The system of claim 1, wherein the emulated neurosensory signal is representative of traffic along an aortic depressor nerve.

7. The system of claim 1, wherein the emulated neurosensory signal represents a recording of the nerve traffic.

8. The system of claim 7, wherein the emulated neurosensory signal is an amplitude-scaled version of the nerve traffic recording.

9. The system of claim 1, wherein the emulated neurosensory signal represents a signal derived from a recording of the nerve traffic.

10. The system of claim 9, wherein the derived signal is a time domain signal produced from an inverse of a mathematical transformation applied to the nerve traffic recording.

11. The system of claim 1, comprising an implantable sensor coupled to the controller, the implantable sensor configured to sense cardiac activity, wherein the controller is configured to modify the emulated neurosensory signal in response to signals produced by the implantable sensor.

12. The system of claim 1, further comprising an aortic balloon pump counter-pulsation system configured to operate cooperatively with the implantable electronic neuromodulation system.

13. A method, comprising:
   storing, in an implantable electronic neuromodulation system, an emulated neurosensory signal representative of nerve traffic acquired from a patient equipped with an extra-aortic balloon pump counter-pulsation system or an intra-aortic balloon pump counter-pulsation system;
   sensing occurrence of a diastolic phase of a patient's heart; and
   stimulating, during the diastolic phase, at least one nerve that carries sensory information from baroreceptors using the emulated neurosensory signal.

14. The method of claim 13, wherein the at least one nerve includes a carotid sinus nerve or an aortic depressor nerve.

15. The method of claim 13, wherein stimulating comprises:
   stimulating a carotid sinus nerve using a first emulated neurosensory signal; and
   stimulating an aortic depressor nerve using a second emulated neurosensory signal.

16. The method of claim 13, further comprising compressing, during the diastolic phase, an ascending aorta of the heart using an extra-aortic balloon pump counter-pulsation system or an intra-aortic balloon pump counter-pulsation system.

17. A system, comprising:
   an implantable stimulation source including a controller configured to control delivery of electrical stimulation modeled to emulate an extra-aortic balloon pump counter-pulsation system or an intra-aortic balloon pump counter-pulsation system;
   a lead coupled to the stimulation source; and
   at least one electrode coupled to the lead, wherein the at least one electrode is positionable in contact with or adjacent to at least one nerve.

18. The system of claim 17, wherein the at least one nerve includes a carotid sinus nerve or an aortic depressor nerve.

19. The system of claim 17, comprising a first electrode and a second electrode respectively coupled to the lead, wherein:
   the first electrode is positionable in contact with or adjacent to a carotid sinus nerve; and the second electrode is positionable in contact with or adjacent to an aortic depressor nerve.

20. The system of claim 17, further comprising an aortic balloon pump counter-pulsation system configured to operate cooperatively with the implantable stimulation source.

* * * * *